(12) United States Patent
Aftab et al.

(10) Patent No.: US 8,901,137 B2
(45) Date of Patent: Dec. 2, 2014

(54) METHODS OF TREATING CANCER USING PYRIDOPYRIMIDINONE INHIBITORS OF PI3K AND MTOR IN COMBINATION WITH AUTOPHAGY INHIBITORS

(75) Inventors: Dana T. Aftab, San Rafael, CA (US); Wolfgang M. Korn, San Anselmo, CA (US); Olga K. Mirzoeva, San Francisco, CA (US)

(73) Assignee: Exelixis, Inc., South San Francisco, CA (US)

( * ) Notice: Subject to any disclaimer, the term of this patent is extended or adjusted under 35 U.S.C. 154(b) by 0 days.

(21) Appl. No.: 13/578,058

(22) PCT Filed: Feb. 9, 2011

(86) PCT No.: PCT/US2011/024187
§ 371 (c)(1),
(2), (4) Date: Mar. 22, 2013

(87) PCT Pub. No.: WO2011/100319
PCT Pub. Date: Aug. 18, 2011

(65) Prior Publication Data
US 2013/0172371 A1 Jul. 4, 2013

Related U.S. Application Data

(60) Provisional application No. 61/367,512, filed on Jul. 26, 2010, provisional application No. 61/367,505, filed on Jul. 26, 2010, provisional application No. 61/302,897, filed on Feb. 9, 2010.

(51) Int. Cl.
*A01N 43/90* (2006.01)
*A61K 31/519* (2006.01)
*A61K 31/4706* (2006.01)
*A61K 35/00* (2006.01)
*A61K 45/06* (2006.01)

(52) U.S. Cl.
CPC ........... *A61K 31/519* (2013.01); *A61K 31/4706* (2013.01); *A61K 35/00* (2013.01); *A61K 45/06* (2013.01)
USPC .................................................... 514/264.11

(58) Field of Classification Search
None
See application file for complete search history.

(56) References Cited

U.S. PATENT DOCUMENTS

| | | | |
|---|---|---|---|
| 7,989,622 B2 | 8/2011 | Bajjalieh et al. | |
| 8,044,062 B2 * | 10/2011 | Baik et al. | 514/264.11 |
| 8,101,622 B2 | 1/2012 | Baik et al. | |
| 8,247,408 B2 | 8/2012 | Baik et al. | |
| 2004/0009993 A1 | 1/2004 | Angiolini et al. | |
| 2005/0182078 A1 | 8/2005 | Barvian et al. | |
| 2010/0075947 A1 | 3/2010 | Aftab et al. | |
| 2010/0087456 A1 * | 4/2010 | Baik et al. | 514/264.11 |
| 2010/0150827 A1 | 6/2010 | Buhr et al. | |
| 2010/0209340 A1 | 8/2010 | Buhr et al. | |
| 2010/0209420 A1 | 8/2010 | Lamb et al. | |
| 2010/0227861 A1 | 9/2010 | Bearss et al. | |
| 2011/0123434 A1 | 5/2011 | Lamb et al. | |
| 2011/0207712 A1 | 8/2011 | Bajjalieh et al. | |
| 2011/0237608 A1 | 9/2011 | Baik et al. | |
| 2012/0302545 A1 | 11/2012 | Aftab et al. | |
| 2013/0172371 A1 | 7/2013 | Aftab et al. | |

FOREIGN PATENT DOCUMENTS

| | | |
|---|---|---|
| EP | 1277738 | 1/2003 |
| EP | 1364950 | 11/2003 |
| JP | 2004083587 | 3/2004 |
| WO | 9634867 | 11/1996 |
| WO | 9833798 | 8/1998 |
| WO | 0155148 | 8/2001 |
| WO | 0170741 | 9/2001 |
| WO | 03088972 | 10/2003 |
| WO | 03093290 | 11/2003 |
| WO | 2004063195 | 7/2004 |
| WO | 2004089930 | 10/2004 |
| WO | 2005040337 | 5/2005 |
| WO | 2005082903 | 9/2005 |
| WO | 2005105097 | 11/2005 |
| WO | 2005105801 | 11/2005 |
| WO | 2006065703 | 6/2006 |
| WO | 2007044813 | 4/2007 |
| WO | 2008021389 | 2/2008 |

OTHER PUBLICATIONS

Zeilhofer et al., Cancer Letters, 1989, 44, 61-66.*
Savarino A et al: "Risks and benefits of chloroiquine use in anticancer strategies", Lancet Oncology, Lancet Publishing Group, London, GB, vol. 7, No. 10, Oct. 1, 2006, pp. 792-793.

(Continued)

*Primary Examiner* — Dennis Heyer
*Assistant Examiner* — Daniel M Podgorski
(74) *Attorney, Agent, or Firm* — Honigman Miller Schwartz and Cohn LLP; Heidi M. Berven; Jonathan P. O'Brien

(57) ABSTRACT

The invention provides compounds of Formula I:

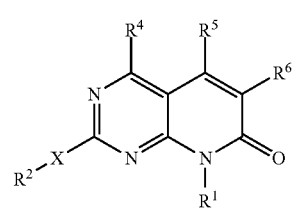

that inhibit the PI3Ks and mTOR that are useful in the treatment of cancer in humans when used in combination with autophagy inhibitors.

1 Claim, 5 Drawing Sheets

(56) References Cited

OTHER PUBLICATIONS

Vezmar M et al: "Reversal of MRP-Mediated doxorubicin resistance with quinoline-based drugs", Biochemical Pharmacology, Pergamon, Oxford, GB, vol. 59, No. 10, May 1, 2000, pp. 1245-1252.
Wang Jianrong et al: "A non-canonical MEK/ERK signaling pathway regulates autophagy via regulating Beclin 1,", The Journal of Biological Chemistry Aug. 7, 2009 LNKD-PUBMED:19520853, vol. 284, No. 32, Aug. 7, 2009, pp. 21412-21424.
International Search Report for PCT/US2011/024187, mailed May 10, 2011.
Griesser, Chapter 8, The Importance of Solvates (pp. 211-230), Polymorphism: In the Pharmaceutical Industry, Hilfiker, 2006.
Wikipedia, Acyl, last modified Mar. 11, 2010.
IUPAC, http://www.iupac.org/goldbook/A00123.pdf, downloaded Oct. 29, 2010.
Hawley's Condensed Chem. Dict., 14th Ed., 2002.
Hackh's Chem. Dict., 3rd Ed., 1944, p. 18.
Angiolini, M., et al., "Solid-phase synthesis of pyrido[2,3-d]pyrimidin-7-ones," Tetrahedron Letters, (2005), vol. 46, pp. 8749-8752.
Barvian, M., et al., "Pyrido[2, 3-d]pyrimidin-7-one inhibitors of cyclin-dependent kinases," J. Med. Chem., (2000) vol. 43, pp. 4606-4616.
Boschelli, D.H., et al., "Synthesis and tyrosine kinase inhibitory activity of a series of 2-amino-8H-pyrido[2, 3-d] pyrimidines: identification of potent, selective platelet-derived growth factor receptor tyrosine kinase inhibitors," J. Med. Chem., (1998) vol. 41, pp. 4365-4377.
Hamby, J.M. et al., "Structure-activity relationships for a novel series of pyrido[2, 3-d]pyrimidine tyrosine kinase inhibitors," J. Med. Chem., (1997) vol. 40, pp. 2296-2303.
Klutchko, S.R., et al., "2-Substituted aminopyrido[2, 3- d]pyrimidin-7(8H)-ones. Structure-activity relationships against selected tyrosine kinases and in vitro and in vivo anticancer activity," J. Med Chem., (1998), vol. 41, pp. 3276-3292.
Toogood, P.L. et al., "Discovery of a potent and selective inhibitor of cyclin-dependent kinase 4/6 ," J. Med. Chem., (2005) vol. 48, pp. 2388-2406.
Trumpp-Kallmeyer, S., et al., "Development of a binding model to protein tyrosine kinases for substituted pyrido[2, 3-d] pyrimidine inhibitors," J. Med. Chem., (1998) vol. 41, pp. 1752-1763.
Database Registry, CAS registration No. 400881-06-3, (date of publication Mar. 14, 2002), Chemical Abstracts Service, STN North America, Columbus, Ohio, www.cas.org/stn.html.
Database Registry, CAS registration No. 400878-58-2, (date of publication Mar. 14, 2002), Chemical Abstracts Service, STN North America, Columbus, Ohio, www.cas.org/stn.html.
Database Registry, CAS registration No. 374910-33-5 (date of publication Dec. 13, 2001), Chemical Abstracts Service, STN North America, Columbus, Ohio, www.cas.org/stn.html.
Database Registry, CAS registration No. 294874-94-5 (date of publication Oct. 12, 2000), Chemical Abstracts Service, STN North America, Columbus, Ohio, www.cas.org/stn.html.
Database Registry, CAS registration No. 405295-77-4 (date of publication Apr. 16, 2002), Chemical Abstracts Service, STN North America, Columbus, Ohio, www.cas.org/stn.html.
Savarino, et al., "Risks and benefits of chloroquine use in anticancer strategies." Lancet Oncology, 7(10):792-793, 2006.
Vezmar, et al., "Reversal of MRP-Mediated doxorubicin resistance with quinoline-based drugs." Biochemical Pharmacology, 59(10): 1245-1252, 2000.
Wang, et al., "A non-canonical MEK/ERK signaling pathway regulates autophagy via regulating Beclin 1." The Journal of Biological Chemistry, 284(32):21412-21424, 2009.
International Search Report for PCT/US2011/024187 mailed May 10, 2011.

* cited by examiner

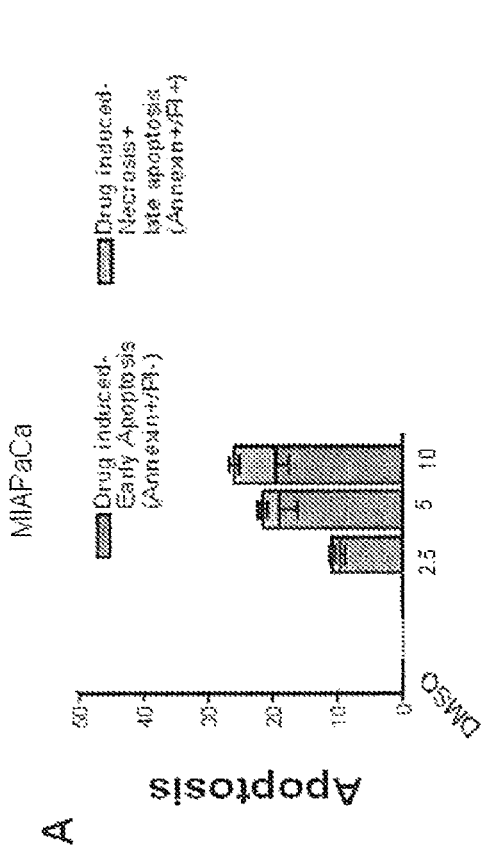
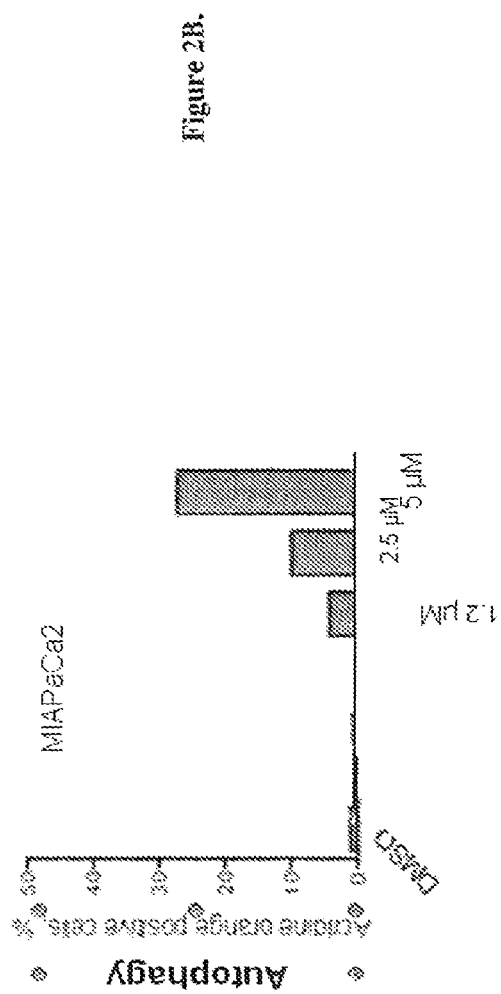
Figure 2A.
Figure 2B.

Figures 4A and B.

181-91; Marsit, Meng et al. *Hum Pathol* 2005, 36(7), 768-76); small cell lung cancer, squamous lung cancer, and adenocarcinoma (Mansion, Taflan et al. *Am J Respir Crit. Care Med* 2004, 170(10), 1088-94); colorectal tumors (Velho, Oliveira et al. *Eur J Cancer* 2005, 41(11), 1649-54; Foukas, Claret et al. *Nature*, 2006, 441(7091), 366-370; Goel, Arnold et al. *Cancer Res* 2004, 64(9), 3014-21; Nassif, Lobo et al. *Oncogene* 2004, 23(2), 617-28; Bos *Cancer Res* 1989. 49(17), 4682-9; Fearon *Ann N Y Acad Sci* 1995, 768, 101-10); gastric carcinomas (Byun, Cho et al. *Int J Cancer* 2003, 104(3), 318-27); hepatocellular tumors (Lee, Soung et al. *Oncogene* 2005, 24(8), 1477-80; Hu, Huang et al. *Cancer* 2003, 97(8), 1929-40; Wan, Jiang et al. *Cancer Res Clin Oncol* 2003, 129(2), 100-6); melanomas (Guldberg, thor Straten et al. *Cancer Res* 1997, 57(17), 3660-3; Tsao, Zhang et al. *Cancer Res* 2000, 60(7), 1800-4; Whiteman, Thou et al. *Int J Cancer* 2002, 99(1), 63-7; Goel, Lazar et al. *J Invest Dermatol* 126(1), 2006, 154-60); pancreatic tumors (Asano, Yao et al. *Oncogene* 2004, 23(53), 8571-80); prostate carcinoma (Cairns, Okami et al. *Cancer Res* 1997, 57(22), 4997-5000; Gray, Stewart et al. *Br J Cancer* 1998, 78(10), 1296-300; Wang, Parsons et al. *Clin Cancer Res* 1998, 4(3), 811-5; Whang, Wu et al. *Proc Natl Acad Sci USA* 1998, 95(9), 5246-50; Majumder and Sellers *Oncogene* 2005, 24(50) 7465-74; Wang, Garcia et al. *Proc Natl Acad Sci USA* 2006, 103(5), 1480-5; Lu, Ren et al. *Int J Oncol* 2006, 28(1), 245-51; Mulholland, Dedhar et al. *Oncogene* 25(3), 2006, 329-37; Xin, Teitell et al. *Proc Nail Acad Sci USA* 2006, 103(20), 7789-94; Mikhailova, Wang et al. *Adv Exp Med Biol* 2008, 617, 397-405; Wang, Mikhailova et al. *Oncogene* 2008, 27(56), 7106-7117); thyroid carcinoma, particularly in the anaplastic subtype (Garcia-Rostan, Costa et al. *Cancer Res* 2005, 65(22), 10199-207); follicular thyroid carcinoma (Wu, Mambo et al. *J Clin Endocrinol Metab* 2005, 90(8), 4688-93); anaplastic large cell lymphoma (ALCL); hamaratomas (including Cowden's disease—multiple hamaratoma syndrome), angiomyelolipomas, TSC-Associated and sporadic lymphangioleiomyomatosis (Bissler, McCormack et al. *N Engl J Med* 2008, 358(2), 140-151); sclerosing hemangioma, a rare lung tumor (Randa M. S. Amin *Pathology International* 2008, 58(1), 38-44; and head and neck cancer (Gupta, McKenna et al. *Clin Cancer Res* 2002, 8(3), 885-892).

In particular, pancreatic cancer remains an incurable disease and current therapies result in only minimal survival benefit. Frequent activation of the PI3 kinase pathway, resulting in part from the ubiquitous presence of activations of KRAS, has been demonstrated in pancreatic ductal adenocarcinomas (PDACs) and found to be correlated with poor outcome after surgery. Constitutive activation of the PI3K pathway is an important consequence of this mutation since this pathway promotes cell survival, growth, and proliferation. Interestingly, upon testing a PI3K/mTOR inhibitor of the present invention in a panel of pancreatic cancer cell lines, Applicants found that apoptotic cell death was preceded by induction of autophagy. Autophagy inhibition resulted in enhancement of apoptosis. In agreement with these findings, the combination of a PI3K/mTOR inhibitor of the present invention with the autophagy inhibitor chloroquine in a xenograft model of pancreatic cancer resulted in significant delay of tumor growth. This suggests a possible role for the PI3Ks and mTOR inhibitors disclosed herein in combination with autophagy inhibitors, in the treatment of pancreatic adenocarcinoma.

SUMMARY OF THE INVENTION

The following only summarizes certain aspects of the invention and is not intended to be limiting in nature. These aspects and other aspects and embodiments are described more fully below. All references cited in this specification are hereby incorporated by reference in their entirety. In the event of a discrepancy between the express disclosure of this specification and the references incorporated by reference, the express disclosure of this specification shall control.

One aspect of the Invention is directed to a method of treating cancer which method comprises administering to a patient a therapeutically effective amount of a Compound of Formula I:

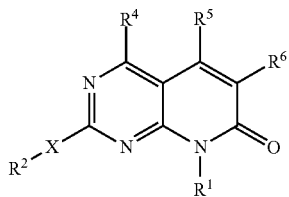

or a single isomer thereof where the compound is optionally as a pharmaceutically acceptable salt and additionally optionally as a hydrate and additionally optionally as a solvate thereof; or administering a pharmaceutical composition comprising a therapeutically effective amount of a Compound of Formula I in combination with one or more autophagy inhibitors, wherein in the Compound of Formula I:

$R^1$ is hydrogen, optionally substituted alkyl, optionally substituted cycloalkyl, optionally substituted cycloalkylalkyl, optionally substituted aryl, optionally substituted arylalkyl, optionally substituted heterocycloalkyl, optionally substituted heterocycloalkylalkyl, optionally substituted heteroaryl or optionally substituted heteroarylalkyl;

$R^2$ is hydrogen or alkyl where the alkyl is optionally substituted with 1, 2, 3, 4, or 5 $R^8$ groups;

X is —$NR^3$—;

$R^3$ hydrogen;

$R^4$ is optionally substituted alkyl;

$R^5$ is hydrogen; and $R^6$ is phenyl, acyl, or heteroaryl wherein the phenyl and heteroaryl are optionally substituted with 1, 2, 3, 4, or 5 $R^9$ groups;

each $R^8$, when present, is independently hydroxy, halo, alkoxy, haloalkoxy, amino, alkylamino, dialkylaminoalkyl, or alkoxyalkylamino; and each $R^9$, when present, is independently halo, alkyl, haloalkyl, alkoxy, haloalkoxy, cyano, amino, alkylamino, dialkylamino, alkoxyalkyl, carboxyalkyl, alkoxycarbonyl, aminoalkyl, cycloalkyl, aryl, arylalkyl, aryloxy, heterocycloalkyl, or heteroaryl and where the cycloalkyl, aryl, heterocycloalkyl, and heteroaryl, each either alone or as part of another group within $R^9$, are independently optionally substituted with 1, 2, 3, or 4 groups selected from halo, alkyl, haloalkyl, hydroxy, alkoxy, haloalkxy, amino, alkylamino, and dialkylamino.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 2A. Induction of apoptosis by Compound A: Induction of apoptosis was determined by FACS analysis following treatment of MiaPaCa2 cells with inhibitors as indicated for 72 hours.

FIG. 2B. Induction of autophagy by Compound A: Induction of autophagy as determined by acridine orange staining and FACS analysis.

DETAILED DESCRIPTION OF THE INVENTION

Abbreviations and Definitions

Figures 1A, 1E:
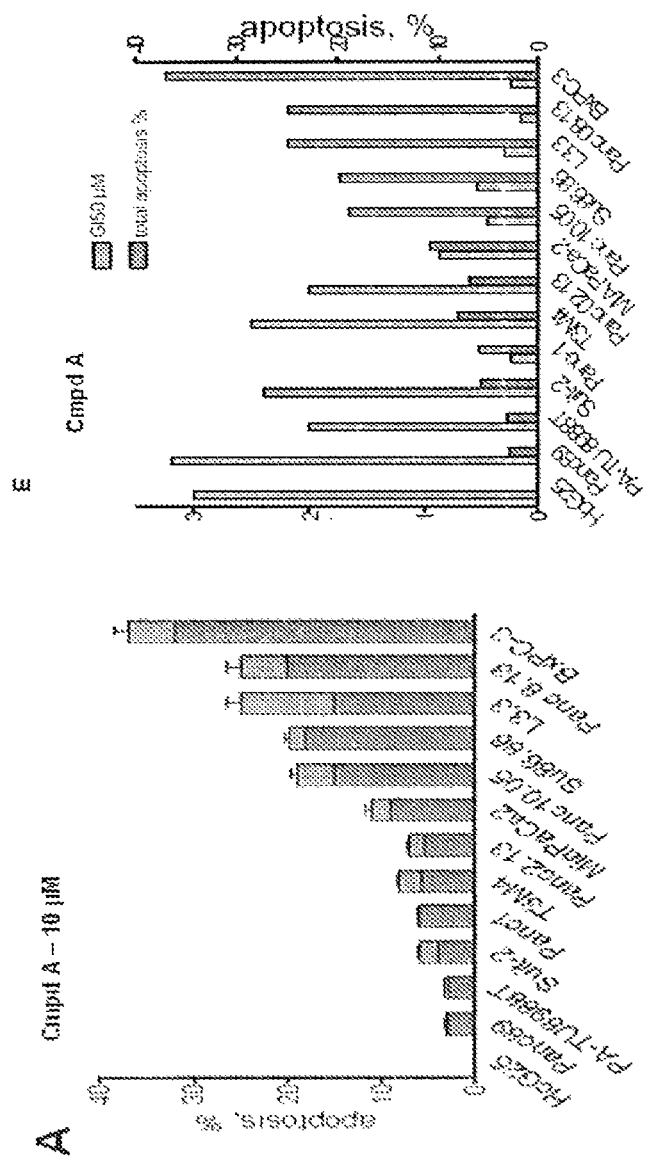
FIG. 1. Apoptosis induction by Compound A: The extent of apoptotis induction in 13 PDAC cell lines to treatment with Compound A is shown in Panel A; Panel E delineates the relationship between GI50 and apoptosis induction for Compound A.

The following abbreviations and terms have the indicated meanings throughout:

| Abbreviation | Meaning |
| --- | --- |
| Ac | acetyl |
| br | broad |
| ° C. | degrees Celsius |
| c- | cyclo |
| CBZ | CarboBenZoxy = benzyloxycarbonyl |
| d | doublet |
| dd | doublet of doublet |
| dt | doublet of triplet |
| DCM | dichloromethane |
| DMA | Dimethylacetamide |
| DME | 1,2-dimethoxyethane |
| DMF | N,N-dimethylformamide |
| DMSO | dimethyl sulfoxide |
| dppf | 1,1'-bis(diphenylphosphano)ferrocene |
| EI | Electron Impact ionization |
| g | gram(s) |
| h or hr | hour(s) |
| HPLC | high pressure liquid chromatography |
| L | liter(s) |
| M | molar or molarity |
| m | Multiplet |
| mg | milligram(s) |
| MHz | megahertz (frequency) |
| Min | minute(s) |
| mL | milliliter(s) |
| μL | microliter(s) |
| μM | Micromole(s) or micromolar |
| mM | Millimolar |
| mmol | millimole(s) |
| mol | mole(s) |
| MS | mass spectral analysis |
| N | normal or normality |
| nM | Nanomolar |
| NMR | nuclear magnetic resonance spectroscopy |
| q | Quartet |
| RT | Room temperature |
| s | Singlet |
| t or tr | Triplet |
| TFA | trifluoroacetic acid |
| THF | tetrahydrofuran |
| TLC | thin layer chromatography |

The symbol "—" means a single bond, "=" means a double bond, "≡" means a triple bond, "====" means a single or double bond. The symbol "〰" refers to a group on a double-bond as occupying either position on the terminus of a double bond to which the symbol is attached; that is, the geometry, E- or Z-, of the double bond is ambiguous. When a group is depicted removed from its parent formula, the "〰" or "—|" symbol will be used at the end of the bond which was theoretically cleaved in order to separate the group from its parent structural formula.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual formula as having a hydrogen or hydrogens as substitution (expressly defined hydrogen), for example, —CH$_2$CH$_2$—. It is understood by one of ordinary skill in the art that the aforementioned descriptive techniques are common in the chemical arts to provide brevity and simplicity to description of otherwise complex structures.

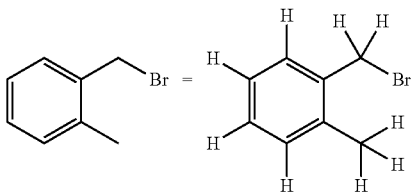

If a group "R" is depicted as "floating" on a ring system, as for example in the formula:

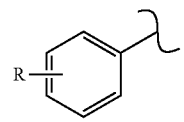

then, unless otherwise defined, a substituent "R" may reside on any atom of the ring system, assuming replacement of a depicted, implied, or expressly defined hydrogen from one of the ring atoms, so long as a stable structure is formed.

If a group "R" is depicted as floating on a fused ring system, as for example in the formulae:

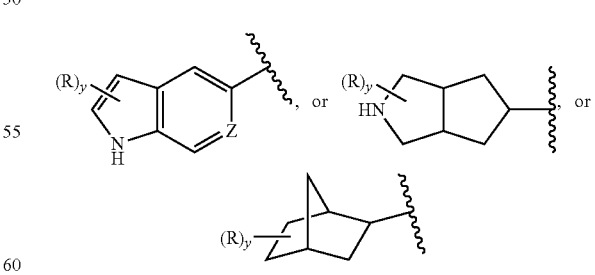

then, unless otherwise defined, a substituent "R" may reside on any atom of the fused ring system, assuming replacement of a depicted hydrogen (for example the —NH— in the formula above), implied hydrogen (for example as in the formula above, where the hydrogens are not shown but understood to be present), or expressly defined hydrogen (for example where in the formula above, "Z" equals =CH—) from one of the ring atoms, so long as a stable structure is formed. In the example depicted, the "R" group may reside on either the 5-membered or the 6-membered ring of the fused ring system. In the formula depicted above, when y is 2 for example, then the two "R's" may reside on any two atoms of the ring system, again assuming each replaces a depicted, implied, or expressly defined hydrogen on the ring.

When a group "R" is depicted as existing on a ring system containing saturated carbons, as for example in the formula:

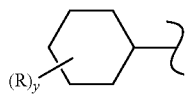

where, in this example, "y" can be more than one, assuming each replaces a currently depicted, implied, or expressly defined hydrogen on the ring; then, unless otherwise defined, where the resulting structure is stable, two "R's" may reside on the same carbon. A simple example is when R is a methyl group; there can exist a geminal dimethyl on a carbon of the depicted ring (an "annular" carbon). In another example, two R's on the same carbon, including that carbon, may form a ring, thus creating a spirocyclic ring (a "spirocyclyl" group) structure with the depicted ring as for example in the formula:

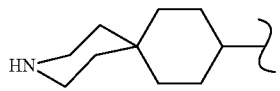

"Acyl" means a —C(O)R radical where R is optionally substituted alkyl, optionally substituted alkenyl, cycloalkyl, cycloalkylalkyl, aryl, aralkyl, heteroaryl, heteroaralkyl, heterocycloalkyl, or heterocycloalkylalkyl, as defined herein, e.g., acetyl, trifluoromethylcarbonyl, or 2-methoxyethylcarbonyl, and the like.

"Acylamino" means a —NRR' radical where R is hydrogen, hydroxy, alkyl, or alkoxy and R' is acyl, as defined herein.

"Acyloxy" means an —OR radical where R is acyl, as defined herein, e.g. cyanomethylcarbonyloxy, and the like.

"Administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., surgery, radiation, and chemotherapy, etc.), "administration" and its variants are each understood to include concurrent and sequential introduction of the compound or prodrug thereof and other agents.

"Alkenyl" means a means a linear monovalent hydrocarbon radical of one to six carbon atoms or a branched monovalent hydrocarbon radical of three to 6 carbon atoms which radical contains at least one double bond, e.g., ethenyl, propenyl, 1-but-3-enyl, and 1-pent-3-enyl, and the like.

"Alkoxy" means an —OR group where R is alkyl group as defined herein. Examples include methoxy, ethoxy, propoxy, isopropoxy, and the like.

"Alkoxyalkyl" means an alkyl group, as defined herein, substituted with at least one, preferably one, two, or three, alkoxy groups as defined herein. Representative examples include methoxymethyl and the like.

"Alkoxyalkylamino" means an NRR' group where R is hydrogen, alkyl, or alkoxyalkyl and R' is alkoxyalkyl, as defined herein.

"Alkoxyalkylaminoalkyl" means an alkyl group substituted with at least one, specifically one or two, alkoxyalkylamino group(s), as defined herein.

"Alkoxycarbonyl" means a —C(O)R group where R is alkoxy, as defined herein.

"Alkyl" means a linear saturated monovalent hydrocarbon radical of one to six carbon atoms or a branched saturated monovalent hydrocarbon radical of three to 6 carbon atoms, e.g., methyl, ethyl, propyl, 2-propyl, butyl (including all isomeric forms), or pentyl (including all isomeric forms), and the like.

"Alkylamino" means an —NHR group where R is alkyl, as defined herein.

"Alkylaminoalkyl" means an alkyl group substituted with one or two alkylamino groups, as defined herein.

"Alkylaminoalkyloxy" means an —OR group where R is alkylaminoalkyl, as defined herein.

"Alkylcarbonyl" means a —C(O)R group where R is alkyl, as defined herein.

"Alkynyl" means a linear monovalent hydrocarbon radical of one to six carbon atoms or a branched monovalent hydrocarbon radical of three to 6 carbon atoms which radical contains at least one triple bond, e.g., ethynyl, propynyl, butynyl, pentyN-2-yl and the like.

"Amino" means —NH$_2$.

"Aminoalkyl" means an alkyl group substituted with at least one, specifically one, two or three, amino groups.

"Aminoalkyloxy" means an —OR group where R is aminoalkyl, as defined herein.

"Aryl" means a monovalent six- to fourteen-membered, mono- or bi-carbocyclic ring, wherein the monocyclic ring is aromatic and at least one of the rings in the bicyclic ring is aromatic. Unless stated otherwise, the valency of the group may be located on any atom of any ring within the radical, valency rules permitting. Representative examples include phenyl, naphthyl, and indanyl, and the like.

"Arylalkyl" means an alkyl radical, as defined herein, substituted with one or two aryl groups, as defined herein, e.g., benzyl and phenethyl, and the like.

"Aryloxy" means an —OR group where R is aryl, as defined herein.

"Autophagy inhibitor" includes, for example, 3-methyladenine (3-MA) and chloroquine (CQ).

"Carboxyalkyl" means an alkyl group, as defined herein, substituted with at least one, specifically one or two, —C(O)OH group(s).

"Cycloalkyl" means a monocyclic or fused bicyclic, saturated or partially unsaturated (but not aromatic), monovalent hydrocarbon radical of three to ten carbon ring atoms. Fused bicyclic hydrocarbon radical includes bridged ring systems. Unless stated otherwise, the valency of the group may be located on any atom of any ring within the radical, valency rules permitting. One or two ring carbon atoms may be replaced by a —C(O)—, —C(S)—, or —C(=NH)— group. More specifically, the term cycloalkyl includes, but is not limited to, cyclopropyl, cyclobutyl, cyclopentyl, cyclohexyl, cyclohexyl, or cyclohex-3-enyl, and the like.

"Cycloalkylalkyl" means an alkyl group substituted with at least one, specifically one or two, cycloalkyl group(s) as defined herein.

"Dialkylamino" means a —NRR' radical where R and R' are alkyl as defined herein, or an N-oxide derivative, or a protected derivative thereof, e.g., dimethylamino, diethylamino, N,N-methylpropylamino or N,N-methylethylamino, and the like.

"Dialkylaminoalkyl" means an alkyl group substituted with one or two dialkylamino groups, as defined herein.

"Dialkylaminoalkyloxy" means an —OR group where R is dialkylaminoalkyl, as defined herein. Representative examples include 2-(N,N-diethylamino)-ethyloxy, and the like.

"Fused-polycyclic" or "fused ring system" means a polycyclic ring system that contains bridged or fused rings; that is, where two rings have more than one shared atom in their ring structures. In this application, fused-polycyclics and fused ring systems are not necessarily all aromatic ring systems. Typically, but not necessarily, fused-polycyclics share a vicinal set of atoms, for example naphthalene or 1,2,3,4-tetrahydro-naphthalene. A spiro ring system is not a fused-polycyclic by this definition, but fused polycyclic ring systems of the invention may themselves have Spiro rings attached thereto via a single ring atom of the fused-polycyclic. In some examples, as appreciated by one of ordinary skill in the art, two adjacent groups on an aromatic system may be fused together to form a ring structure. The fused ring structure may contain heteroatoms and may be optionally substituted with one or more groups. It should additionally be noted that saturated carbons of such fused groups (i.e. saturated ring structures) can contain two substitution groups.

"Halogen" or "halo" refers to fluorine, chlorine, bromine or iodine.

"Haloalkoxy" means an —OR' group where R' is haloalkyl as defined herein, e.g., trifluoromethoxy or 2,2,2-trifluoroethoxy, and the like.

"Haloalkyl" mean an alkyl group substituted with one or more halogens, specifically one to five halo atoms, e.g., trifluoromethyl, 2-chloroethyl, and 2,2-difluoroethyl, and the like.

"Heteroaryl" means a monocyclic, fused bicyclic, or fused tricyclic, monovalent radical of 5 to 14 ring atoms containing one or more, specifically one, two, three, or four ring heteroatoms independently selected from —O—, —S(O)$_N$ (n is 0, 1, or 2), —N—, —N(R$^x$)—, and the remaining ring atoms being carbon, wherein the ring comprising a monocyclic radical is aromatic and wherein at least one of the fused rings comprising a bicyclic or tricyclic radical is aromatic. One or two ring carbon atoms of any nonaromatic rings comprising a bicyclic or tricyclic radical may be replaced by a —C(O)—, —C(S)—, or —C(=NH)— group. R$^x$ is hydrogen, alkyl, hydroxy, alkoxy, acyl, or alkylsulfonyl. Fused bicyclic radical includes bridged ring systems. Unless stated otherwise, the valency may be located on any atom of any ring of the heteroaryl group, valency rules permitting. When the point of valency is located on the nitrogen, R$^x$ is absent. More specifically, the term heteroaryl includes, but is not limited to, 1,2,4-triazolyl, 1,3,5-triazolyl, phthalimidyl, pyridinyl, pyrrolyl, imidazolyl, thienyl, furanyl, indolyl, 2,3-dihydro-1H-indolyl (including, for example, 2,3-dihydro-1H-indol-2-yl or 2,3-dihydro-1H-indol-5-yl, and the like), isoindolyl, indolinyl, isoindolinyl, benzimidazolyl, benzodioxol-4-yl, benzofuranyl, cinnolinyl, indolizinyl, naphthyridin-3-yl, phthalazin-3-yl, phthalazin-4-yl, pteridinyl, purinyl, quinazolinyl, quinoxalinyl, tetrazolyl, pyrazolyl, pyrazinyl, pyrimidinyl, pyridazinyl, oxazolyl, isooxazolyl, oxadiazolyl, benzoxazolyl, quinolinyl, isoquinolinyl, tetrahydroisoquinolinyl (including, for example, tetrahydroisoquinolin-4-yl or tetrahydroisoquinolin-6-yl, and the like), pyrrolo[3,2-c]pyridinyl (including, for example, pyrrolo[3,2-c]pyridin-2-yl or pyrrolo[3,2-c]pyridin-7-yl, and the like), benzopyranyl, thiazolyl, isothiazolyl, thiadiazolyl, benzothiazolyl, benzothienyl, and the derivatives thereof, or N-oxide or a protected derivative thereof.

"Heteroarylalkyl" means an alkyl group, as defined herein, substituted with at least one, specifically one or two heteroaryl group(s), as defined herein.

"Heteroatom" refers to O, S, N, or P.

"Heterocycloalkyl" means a saturated or partially unsaturated (but not aromatic) monovalent monocyclic group of 3 to 8 ring atoms or a saturated or partially unsaturated (but not aromatic) monovalent fused bicyclic group of 5 to 12 ring atoms in which one or more, specifically one, two, three, or four ring heteroatoms independently selected from O, S(O)$_n$ (n is 0, 1, or 2), N, N(R$^y$) (where R$^y$ is hydrogen, alkyl, hydroxy, alkoxy, acyl, or alkylsulfonyl), the remaining ring atoms being carbon. One or two ring carbon atoms may be replaced by a —C(O)—, —C(S)—, or —C(=NH)— group. Fused bicyclic radical includes bridged ring systems. Unless otherwise stated, the valency of the group may be located on any atom of any ring within the radical, valency rules permitting. When the point of valency is located on a nitrogen atom, R$^y$ is absent. More specifically the term heterocycloalkyl includes, but is not limited to, azetidinyl, pyrrolidinyl, 2-oxopyrrolidinyl, 2,5-dihydro-1H-pyrrolyl, piperidinyl, 4-piperidonyl, morpholinyl, piperazinyl, 2-oxopiperazinyl, tetrahydropyranyl, 2-oxopiperidinyl, thiomorpholinyl, thiamorpholinyl, perhydroazepinyl, pyrazolidinyl, imidazolinyl, imidazolidinyl, dihydropyridinyl, tetrahydropyridinyl, oxazolinyl, oxazolidinyl, isoxazolidinyl, thiazolinyl, thiazolidinyl, quinuclidinyl, isothiazolidinyl, octahydroindolyl, octahydroisoindolyl, decahydroisoquinolyl, tetrahydrofuryl, and tetrahydropyranyl, and the derivatives thereof and N-oxide or a protected derivative thereof.

"Heterocycloalkylalkyl" means an alkyl radical, as defined herein, substituted with one or two heterocycloalkyl groups, as defined herein, e.g., morpholinylmethyl, N-pyrrolidinylethyl, and 3-(N-azetidinyl)propyl, and the like.

"Heterocycloalkylalkyloxy means an —OR group where R is heterocycloalkylalkyl, as defined herein.

"Saturated bridged ring system" refers to a bicyclic or polycyclic ring system that is not aromatic. Such a system may contain isolated or conjugated unsaturation, but not aromatic or heteroaromatic rings in its core structure (but may have aromatic substitution thereon). For example, hexahydro-furo[3,2-b]furan, 2,3,3a,4,7,7a-hexahydro-1H-indene, 7-aza-bicyclo[2.2.1]heptane, and 1,2,3,4,4a,5,8,8a-octahydro-naphthalene are all included in the class "saturated bridged ring system.

"Spirocyclyl" or "spirocyclic ring" refers to a ring originating from a particular annular carbon of another ring. For example, as depicted below, a ring atom of a saturated bridged ring system (rings B and B'), but not a bridgehead atom, can be a shared atom between the saturated bridged ring system and a spirocyclyl (ring A) attached thereto. A spirocyclyl can be carbocyclic or heteroalicyclic.

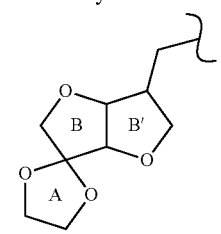

"Optional" or "optionally" means that the subsequently described event or circumstance may or may not occur, and that the description includes instances where said event or circumstance occurs and instances in which it does not. One of ordinary skill in the art would understand that with respect to any molecule described as containing one or more optional substituents, only sterically practical and/or synthetically feasible compounds are meant to be included. "Optionally substituted" refers to all subsequent modifiers in a term. So, for example, in the term "optionally substituted aryl$C_{1-8}$ alkyl," optional substitution may occur on both the "$C_{1-8}$ alkyl" portion and the "aryl" portion of the molecule may or may not be substituted. A list of exemplary optional substitutions is presented below in the definition of "substituted."

"Optionally substituted alkoxy" means an —OR group where R is optionally substituted alkyl, as defined herein.

"Optionally substituted alkyl" means an alkyl radical, as defined herein, optionally substituted with one or more group(s), specifically one, two, three, four, or five groups, independently selected from alkylcarbonyl, alkenylcarbonyl, cycloalkylcarbonyl, alkylcarbonyloxy, alkenylcarbonyloxy, amino, alkylamino, dialkylamino, aminocarbonyl, alkylaminocarbonyl, dialkylaminocarbonyl, cyano, cyanoalkylaminocarbonyl, alkoxy, alkenyloxy, hydroxy, hydroxyalkoxy, halo, carboxy, alkylcarbonylamino, alkylcarbonyloxy, alkyl-$S(O)_{0-2}$—, alkenyl-$S(O)_{0-2}$—, aminosulfonyl, alkylaminosulfonyl, dialkylaminosulfonyl, alkylsulfonyl-$NR^c$— (where $R^c$ is hydrogen, alkyl, optionally substituted alkenyl, hydroxy, alkoxy, alkenyloxy, or cyanoalkyl), alkylaminocarbonyloxy, dialkylaminocarbonyloxy, alkylaminoalkyloxy, dialkylaminoalkyloxy, alkoxycarbonyl, alkenyloxycarbonyl, alkoxycarbonylamino, alkylaminocarbonylamino, dialkylaminocarbonylamino, alkoxyalkyloxy, and —$C(O)NR^aR^b$ (where $R^a$ and $R^b$ are independently hydrogen, alkyl, optionally substituted alkenyl, hydroxy, alkoxy, alkenyloxy, or cyanoalkyl).

"Optionally substituted alkenyl" means an alkyl radical, as defined herein, optionally substituted with one or more group(s), specifically one, two, three, four, or five groups, independently selected from alkylcarbonyl, alkenylcarbonyl, cycloalkylcarbonyl, alkylcarbonyloxy, alkenylcarbonyloxy, amino, alkylamino, dialkylamino, aminocarbonyl, alkylaminocarbonyl, dialkylaminocarbonyl, cyano, cyanoalkylaminocarbonyl, alkoxy, alkenyloxy, hydroxy, hydroxyalkoxy, halo, carboxy, alkylcarbonylamino, alkylcarbonyloxy, alkyl-$S(O)_{0-2}$—, alkenyl-$S(O)_{0-2}$—, aminosulfonyl, alkylaminosulfonyl, dialkylaminosulfonyl, alkylsulfonyl-$NR^c$— (where $R^c$ is hydrogen, alkyl, optionally substituted alkenyl, hydroxy, alkoxy, alkenyloxy, or cyanoalkyl), alkylaminocarbonyloxy, dialkylaminocarbonyloxy, alkylaminoalkyloxy, dialkylaminoalkyloxy, alkoxycarbonyl, alkenyloxycarbonyl, alkoxycarbonylamino, alkylaminocarbonylamino, dialkylaminocarbonylamino, alkoxyalkyloxy, and —$C(O)NR^aR^b$ (where $R^a$ and $R^b$ are independently hydrogen, alkyl, optionally substituted alkenyl, hydroxy, alkoxy, alkenyloxy, or cyanoalkyl).

"Optionally substituted amino" refers to the group —N(H)R or —N(R)R where each R is independently selected from the group: optionally substituted alkyl, optionally substituted alkoxy, optionally substituted aryl, optionally substituted heterocycloalkyl, optionally substituted heteroaryl, acyl, carboxy, alkoxycarbonyl, —$S(O)_2$-(optionally substituted alkyl), —$S(O)_2$-optionally substituted aryl), —$S(O)_2$-(optionally substituted heterocycloalkyl), —$S(O)_2$-(optionally substituted heteroaryl), and —$S(O)_2$-(optionally substituted heteroaryl). For example, "optionally substituted amino" includes diethylamino, methylsulfonylamino, and furanyl-oxy-sulfonamino.

"Optionally substituted aminoalkyl" means an alkyl group, as defined herein, substituted with at least one, specifically one or two, optionally substituted amino group(s), as defined herein.

"Optionally substituted aryl" means an aryl group, as defined herein, optionally substituted with one, two, or three substituents independently selected from acyl, acylamino, acyloxy, optionally substituted alkyl, optionally substituted alkenyl, alkoxy, alkenyloxy, halo, hydroxy, alkoxycarbonyl, alkenyloxycarbonyl, amino, alkylamino, dialkylamino, nitro, aminocarbonyl, alkylaminocarbonyl, dialkylaminocarbonyl, carboxy, cyano, alkylthio, alkylsulfinyl, alkylsulfonyl, aminosulfonyl, alkylaminosulfonyl, dialkylaminosulfonyl, alkylsulfonylamino, aminoalkoxy, or aryl is pentafluorophenyl. Within the optional substituents on "aryl", the alkyl and alkenyl, either alone or as part of another group (including, for example, the alkyl in alkoxycarbonyl), are independently optionally substituted with one, two, three, four, or five halo.

"Optionally substituted arylalkyl" means an alkyl group, as defined herein, substituted with optionally substituted aryl, as defined herein.

"Optionally substituted cycloalkyl" means a cycloalkyl group, as defined herein, substituted with one, two, or three groups independently selected from acyl, acyloxy, acylamino, optionally substituted alkyl, optionally substituted alkenyl, alkoxy, alkenyloxy, alkoxycarbonyl, alkenyloxycarbonyl, alkylthio, alkylsulfinyl, alkylsulfonyl, aminosulfonyl, alkylaminosulfonyl, dialkylaminosulfonyl, alkylsulfonylamino, halo, hydroxy, amino, alkylamino, dialkylamino, aminocarbonyl, alkylaminocarbonyl, dialkylaminocarbonyl, nitro, alkoxyalkyloxy, aminoalkoxy, alkylaminoalkoxy, dialkylaminoalkoxy, carboxy, and cyano. Within the above optional substitutents on "cycloalkyl", the alkyl and alkenyl, either alone or as part of another substituent on the cycloalkyl ring, are independently optionally substituted with one, two, three, four, or five halo, e.g. haloalkyl, haloalkoxy, haloalkenyloxy, or haloalkylsulfonyl.

"Optionally substituted cycloalkylalkyl" means an alkyl group substituted with at least one, specifically one or two, optionally substituted cycloalkyl groups, as defined herein.

"Optionally substituted heteroaryl" means a heteroaryl group optionally substituted with one, two, or three substituents independently selected from acyl, acylamino, acyloxy, optionally substituted alkyl, optionally substituted alkenyl, alkoxy, alkenyloxy, halo, hydroxy, alkoxycarbonyl, alkenyloxycarbonyl, amino, alkylamino, dialkylamino, nitro, aminocarbonyl, alkylaminocarbonyl, dialkylaminocarbonyl, carboxy, cyano, alkylthio, alkylsulfinyl, alkylsulfonyl, aminosulfonyl, alkylaminosulfonyl, dialkylaminosulfonyl, alkylsulfonylamino, aminoalkoxy, alkylaminoalkoxy, and dialkylaminoalkoxy. Within the optional substituents on "heteroaryl", the alkyl and alkenyl, either alone or as part of another group (including, for example, the alkyl in alkoxycarbonyl), are independently optionally substituted with one, two, three, four, or five halo.

"Optionally substituted heteroarylalkyl" means an alkyl group, as defined herein, substituted with at least one, specifically one or two, optionally substituted heteroaryl group(s), as defined herein.

"Optionally substituted heterocycloalkyl" means a heterocycloalkyl group, as defined herein, optionally substituted with one, two, or three substituents independently selected from acyl, acylamino, acyloxy, optionally substituted alkyl, optionally substituted alkenyl, alkoxy, alkenyloxy, halo, hydroxy, alkoxycarbonyl, alkenyloxycarbonyl, amino, alkylamino, dialkylamino, nitro, aminocarbonyl, alkylaminocarbonyl, dialkylaminocarbonyl, carboxy, cyano, alkylthio, alkylsulfinyl, alkylsulfonyl, aminosulfonyl, alkylaminosulfonyl, dialkylaminosulfonyl, alkylsulfonylamino, aminoalkoxy, or aryl is pentafluorophenyl. Within the optional substituents on "heterocycloalkyl", the alkyl and alkenyl, either alone or as part of another group (including, for example, the alkyl in alkoxycarbonyl), are independently optionally substituted with one, two, three, four, or five halo.

"Optionally substituted heterocycloalkylalkyl" means an alkyl group, as defined herein, substituted with at least one, specifically one or two, optionally substituted heterocycloalkyl group(s) as defined herein.

As used herein, "Compound A" means the structure

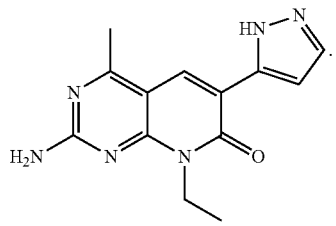 [SMILES: CCn1c(=O)c(-c2ccn[nH]2)cc2c(C)nc(N)nc21]

"Pharmaceutical composition" comprises 1) a Compound of Formula I or a single isomer thereof where the compound is optionally as a pharmaceutically acceptable salt and additionally optionally as a hydrate and additionally optionally as a solvate thereof; 2) a pharmaceutically acceptable carrier, excipient, or diluent, and 3) optionally an autophagy inhibitor as described herein.

"Yield" for each of the reactions described herein is expressed as a percentage of the theoretical yield.

"Patient" for the purposes of the present invention includes humans and other animals, particularly mammals, and other organisms. Thus the methods are applicable to both human therapy and veterinary applications. In a preferred embodiment the patient is a mammal, and in a most preferred embodiment the patient is human.

"Therapeutically effective amount" is an amount of a Compound of Formula I optionally in combination with an autophagy inhibitor, that when administered to a patient, ameliorates a symptom of the disease. The amount of a Compound of Formula I which constitutes a "therapeutically effective amount" will vary depending on the compound, the disease state and its severity, the age of the patient to be treated, and the like. The therapeutically effective amount can be determined routinely by one of ordinary skill in the art having regard to their knowledge and to this disclosure.

A "pharmaceutically acceptable salt" of a compound means a salt that is pharmaceutically acceptable and that possesses the desired pharmacological activity of the parent compound. It is understood that the pharmaceutically acceptable salts are non-toxic. Additional information on suitable pharmaceutically acceptable salts can be found in Remington's Pharmaceutical Sciences, 17$^{th}$ ed., Mack Publishing Company, Easton, Pa., 1985, which is incorporated herein by reference or S. M. Berge, et al., "Pharmaceutical Salts," J. Pharm. Sci., 1977; 66:1-19 both of which are incorporated herein by reference.

Examples of pharmaceutically acceptable acid addition salts include those formed with inorganic acids such as hydrochloric acid, hydrobromic acid, sulfuric acid, nitric acid, phosphoric acid, and the like; as well as organic acids such as acetic acid, trifluoroacetic acid, propionic acid, hexanoic acid, cyclopentanepropionic acid, glycolic acid, pyruvic acid, lactic acid, oxalic acid, maleic acid, malonic acid, succinic acid, fumaric acid, tartaric acid, citric acid, benzoic acid, cinnamic acid, 3-(4-hydroxybenzoyl)benzoic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, p-toluenesulfonic acid, and salicylic acid and the like.

Examples of a pharmaceutically acceptable base addition salts include those formed when an acidic proton present in the parent compound is replaced by a metal ion, such as sodium, potassium, lithium, ammonium, calcium, magnesium, iron, zinc, copper, manganese, aluminum salts and the like. Preferable salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins. Examples of organic bases include isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, tromethamine, N-methylglucamine, polyamine resins, and the like. Exemplary organic bases are isopropylamine, diethylamine, ethanolamine, trimethylamine, dicyclohexylamine, choline, and caffeine.

"Prodrug" refers to compounds that are transformed (typically rapidly) in vivo to yield the parent compound of the above formulae, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention may be prepared according to conventional methods. A thorough discussion of prodrugs is provided in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 8.sup.th Ed., Pergamon Press, Gilman et al. (eds.), 1990 for a discussion of biotransformation). As used herein, the metabolite of a compound of the invention or its salt may be the biologically active form of the compound in the body. In one example, a prodrug may be used such that the biologically active form, a metabolite, is released in vivo. In another example, a biologically active metabolite is discovered serendipitously, that is, no prodrug design per se was undertaken. An assay for activity of a metabolite of a compound of the present invention is known to one of skill in the art in light of the present disclosure.

"Treating" or "treatment" of a disease, disorder, or syndrome, as used herein, includes (i) preventing the disease, disorder, or syndrome from occurring in a human, i.e. causing the clinical symptoms of the disease, disorder, or syndrome not to develop in an animal that may be exposed to or predisposed to the disease, disorder, or syndrome but does not yet experience or display symptoms of the disease, disorder, or syndrome; (ii) inhibiting the disease, disorder, or syndrome, i.e., arresting its development; and (iii) relieving the disease, disorder, or syndrome, i.e., causing regression of the disease, disorder, or syndrome. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

Embodiments of the Invention

The following paragraphs present a number of embodiments that can be used to practice the invention. In each instance, the embodiment includes both the recited compounds as well as individual isomers and mixtures of isomers. In addition, in each instance, the embodiment includes the pharmaceutically acceptable salts, hydrates, and/or solvates of the recited compounds and any individual isomers or mixture of isomers thereof.

In one embodiment (1), the invention is directed to a method of treating cancer which method comprises administering to a patient a therapeutically effective amount of a Compound of Formula I or a pharmaceutical composition comprising a Compound of Formula I, where the Compound of Formula I is as defined in the Summary of the Invention; in combination with one or more autophagy inhibitors.

In another embodiment (2), the invention is directed to a method of treating cancer which method comprises administering to a patient a therapeutically effective amount of a Compound of Formula I or a pharmaceutical composition comprising a Compound of Formula I, where the Compound of Formula I is as defined in the Summary of the Invention; in combination with one or more autophagy inhibitors where the cancer is selected from breast cancer, colon cancer, rectal cancer, endometrial cancer, gastric carcinoma, glioblastoma, hepatocellular carcinoma, small cell lung cancer, non-small cell lung cancer, melanoma, ovarian cancer, cervical cancer, pancreatic cancer, prostate carcinoma, acute myelogenous leukemia (AML), chronic myelogenous leukemia (CML), and thyroid carcinoma. In a subembodiment (2a) of embodiment 2, the cancer is pancreatic cancer.

In another embodiment (3), the invention is directed to a method of treating cancer which method comprises administering to a patient a therapeutically effective amount of a Compound of Formula I or a pharmaceutical composition comprising a Compound of Formula I, where the Compound of Formula I is as defined in the Summary of the Invention; in combination with one autophagy inhibitor. In a subembodiment (3a) of embodiment (3), the autophagy inhibitor is selected from 3-methyladenine and chloroquine.

In another embodiment (4), the method of embodiment 2 or 2a is that where the Compound of Formula I is used in combination with one autophagy inhibitor and the autophagy inhibitor is 3-methyladenine.

In another embodiment (5), the method of embodiment 2 or 2a is that where the Compound of Formula I is used in combination with one autophagy inhibitor and the autophagy inhibitor is chloroquine.

Any of the following embodiments, including the representative compounds in Table 1, may be used to practice any of embodiments 1, 2, 2a, 3, 3a, 4, and 5.

One embodiment (A) of the Invention is directed to a Compound of Formula I where $R^1$ is hydrogen, optionally substituted alkyl, optionally substituted cycloalkyl, optionally substituted cycloalkylalkyl, optionally substituted aryl, optionally substituted arylalkyl, optionally substituted heterocycloalkyl, optionally substituted heterocycloalkylalkyl, optionally substituted heteroaryl or optionally substituted heteroarylalkyl. Specifically. $R^1$ is hydrogen, optionally substituted alkyl, optionally substituted cycloalkyl, optionally substituted arylalkyl, or optionally substituted heterocycloalkylalkyl. More specifically, $R^1$ is hydrogen, alkyl, alkyl substituted with one or two hydroxy, alkyl substituted with alkoxy, cycloalkyl, arylalkyl, or heterocycloalkylalkyl. Even more specifically, $R^1$ is hydrogen, methyl, ethyl, propyl, isopropyl, 2-hydroxypropyl, 3-hydroxypropyl, 2-ethoxyethyl, 3-methoxypropyl, 3-ethoxypropyl, 3-isopropoxypropyl, cyclopropyl, cyclobutyl, cyclopentyl, cyclohexyl, benzyl, or 2-piperidin-1-ylethyl. Yet even more specifically, $R^1$ is ethyl, isopropyl, cyclopentyl, or cyclohexyl. Yet even more specifically, $R^1$ is ethyl.

Another embodiment (B) of the Invention is directed to a Compound of Formula I where $R^2$ is hydrogen or alkyl where the alkyl is optionally substituted with 1, 2, 3, 4, or 5 $R^8$ groups. Specifically, $R^2$ is hydrogen or alkyl where the alkyl is optionally substituted with one, two, or three $R^8$ groups. More specifically, $R^2$ is hydrogen or alkyl where the alkyl is optionally substituted with one, two, or three $R^8$ groups; and each $R^8$, when present, is independently selected from amino, alkylamino, dialkylamino, and halo. Even more specifically, $R^2$ is hydrogen, methyl, ethyl, propyl, isopropyl, tert-butyl, 3-aminopropyl, 3-(N-methylamino)-propyl, 3-(N,N-dimethylamino)-propyl, 2-fluoroethyl, or 2,2,2-trifluoroethyl. Yet even more specifically, $R^2$ is hydrogen or ethyl. Yet even more preferably, $R^2$ is hydrogen.

In another embodiment of the Invention, $R^2$ is hydrogen.

In another embodiment of the invention, $R^2$ is alkyl optionally substituted with 1, 2, 3, 4, or 5, $R^8$ groups. Specifically, $R^2$ is alkyl where the alkyl is optionally substituted with one, two, or three $R^8$ groups; and each $R^8$, when present, is independently selected from amino, alkylamino, dialkylamino, and halo. Even more specifically, $R^2$ is methyl, ethyl, propyl, isopropyl, tert-butyl, 3-aminopropyl, 3-(N-methylamino)-propyl, 3-(N,N-dimethylamino)-propyl, 2-fluoroethyl, or 2,2,2-trifluoroethyl. Yet even more specifically, $R^2$ is ethyl.

Another embodiment (C) of the Invention is directed to a Compound of Formula I where $R^4$ is optionally substituted alkyl. Specifically, $R^4$ is methyl or ethyl. More specifically, $R^4$ is methyl.

Another embodiment (D) of the Invention is directed to a Compound of Formula I where $R^6$ is acyl. More specifically, $R^6$ is alkylcarbonyl. Even more specifically, $R^6$ is acetyl.

Another embodiment (E) of the Invention is directed to a Compound of Formula I where $R^6$ is phenyl optionally substituted with 1, 2, 3, 4, or 5 $R^9$ groups. Specifically, $R^6$ is phenyl optionally substituted with one or two $R^9$ groups; and each $R^9$, when present, is independently selected from aryl, halo, alkoxy, aryloxy, and haloalkyl. More specifically, $R^6$ is phenyl optionally substituted with one or two $R^9$ groups; and each $R^9$, when present, is independently selected from phenyl, fluoro, chloro, methoxy, phenyloxy, and trifluoromethyl. Even more specifically, $R^6$ is phenyl, phenyl substituted with phenyl, fluorophenyl, difluorophenyl, chlorophenyl, dichlorophenyl, phenyl substituted with chloro and fluoro, methoxyphenyl, dimethoxyphenyl, phenyloxyphenyl, or trifluoromethylphenyl. Yet even more specifically, $R^6$ is phenyl, 2-phenyl-phenyl, 3-phenyl-phenyl, 4-phenyl-phenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 3,5-difluorophenyl, 2-chlorophenyl, 3-chlorophenyl, 4-chlorophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 3-chloro-4-fluorophenyl, 2-methoxyphenyl, 3-methoxyphenyl, 4-methoxyphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 4-phenyloxyphenyl, 2-trifluoromethylphenyl, 3-trifluoromethylphenyl, or 4-trifluoromethylphenyl.

Another embodiment (F) of the Invention is directed to a Compound of Formula I where $R^6$ is phenyl substituted with 1, 2, 3, 4, or 5 $R^9$ groups.

Another embodiment (G) of the Invention is directed to a Compound of Formula I where $R^6$ is heteroaryl optionally substituted with 1, 2, 3, 4, or 5 $R^9$ groups.

A more specific embodiment (G1) of embodiment G is a Compound of Formula I where $R^6$ is a 6-membered heteroaryl optionally substituted with one or two $R^9$. More specifically, $R^6$ is pyridinyl, pyrazinyl, pyrimidinyl, or pyridazinyl each of which is optionally substituted with one $R^9$ where $R^9$, when present, is halo. Even more specifically, $R^6$ is pyridiN-2-yl, pyridiN-3-yl, pyridiN-4-yl, 3-fluoropyridiN-4-yl, pyrazin-2-yl, pyrazin-3-yl, pyrimidin-2-yl, pyrimidin-4-yl, pyrimidin-5-yl, pyridazin-3-yl, or pyridazin-4-yl, each of which is optionally substituted with one or two $R^9$.

In an even more specific embodiment (G2) of embodiment G is a Compound of Formula I where $R^6$ is pyrazinyl, pyrimidinyl, or pyridazinyl each of which is optionally substituted with one $R^9$ where $R^9$, when present, is halo. Even more specifically, $R^6$ is pyrazin-2-yl, pyrazin-3-yl, pyrimidin-2-yl, pyrimidin-4-yl, pyrimidin-5-yl, pyridazin-3-yl, or pyridazin-4-yl.

A more specific embodiment (G3) of embodiment G is a Compound of Formula I where $R^6$ is 5-membered heteroaryl optionally substituted with one or two $R^9$. Specifically $R^6$ is pyrazolyl, imidazolyl, thienyl, thiazolyl, oxazolyl, isoxazolyl, oxadiazolyl, furanyl, pyrrolyl, triazolyl, or tetrazolyl, each of which is optionally substituted with one $R^9$ where $R^9$, when present, is alkyl, arylalkyl, cyano, aryl, alkoxycarbonyl, or halo. More specifically, $R^6$ is pyrazol-1-yl, pyrazol-3-yl, pyrazol-4-yl, pyrazol-5-yl, imidazol-1-yl, imidazol-2-yl, imidazol-4-yl, imidazol-5-yl, thien-2-yl, thien-3-yl, thiazol-2-yl, thiazol-4-yl, thiazol-5-yl, oxazol-2-yl, oxazol-4-yl, oxazol-5-yl, isoxazol-3-yl, isoxazol-4-yl, isoxazol-5-yl, 1,2,3-oxadiazol-4-yl, 1,2,3-oxadiazol-5-yl, 1,3,4-oxadiazol-2-yl, 1,2,4-oxadiazol-3-yl, 1,2,4-oxadiazol-5-yl, furan-2-yl, furan-3-yl, pyrrol-1-yl, pyrrol-2-yl, pyrrol-3-yl, triazol-1-yl, triazol-4-yl, triazol-5-yl, tetrazol-1-yl, or tetrazol-5-yl; each of which is optionally substituted with one $R^9$ where $R^9$, when present, is methyl, benzyl, cyano, phenyl, N-tert-butoxycarbonyl, or chloro. Even more specifically, $R^6$ is pyrazol-3-yl, pyrazol-4-yl, pyrazol-5-yl, imidazol-2-yl, imidazol-4-yl, imidazol-5-yl, thien-2-yl, thien-3-yl, thiazol-2-yl, thiazol-4-yl, thiazol-5-yl, oxazol-2-yl, oxazol-4-yl, oxazol-5-yl, isox- azol-3-yl, isoxazol-4-yl, isoxazol-5-yl, 1,2,3-oxadiazol-4-yl, 1,2,3-oxadiazol-5-yl, 1,3,4-oxadiazol-2-yl, 1,2,4-oxadiazol-3-yl, 1,2,4-oxadiazol-5-yl, furan-2-yl, furan-3-yl, pyrrol-2-yl, pyrrol-3-yl, triazol-4-yl, triazol-5-yl, or tetrazol-5-yl; each of which is optionally substituted with one $R^9$ where $R^9$, when present, is methyl, benzyl, cyano, phenyl, N-tert-butoxycarbonyl, or chloro.

A more specific embodiment (G4) of embodiment G is a Compound of Formula I where $R^6$ is thienyl, pyrrolyl, furanyl, pyrazolyl, thiazolyl, isoxazolyl, imidazolyl, triazolyl, or tetrazolyl, each of which is optionally substituted with one $R^9$ where $R^9$, when present, is methyl, benzyl, cyano, phenyl, N-tert-butoxycarbonyl, or chloro. Specifically, $R^6$ is thien-2-yl, thien-3-yl, pyrrol-2-yl, furan-2-yl, furan-3-yl, pyrazol-3-yl, pyrazol-4-yl, pyrazol-5-yl, thiazol-2-yl, thiazol-5-yl, isoxazol-4-yl, imidazol-5-yl, triazol-5-yl, tetrazol-5-yl, each of which is optionally substituted with one $R^9$ where $R^9$, when present, is methyl, benzyl, cyano, phenyl, N-tert-butoxycarbonyl, or chloro. More specifically, $R^6$ is thien-2-yl, thien-3-yl, 5-cyano-thien-2-yl, 4-methyl-thien-2-yl, 4-methyl-thien-3-yl, 5-chloro-thien-5-yl, 5-phenyl-thien-2-yl, pyrrol-2-yl, N-tert-butoxycarbonyl-pyrrol-2-yl, N-methyl-pyrrol-2-yl, furan-2-yl, furan-3-yl, pyrazol-3-yl, pyrazol-4-yl, N-benzyl-pyrazol-4-yl, pyrazol-5-yl, thiazol-2-yl, thiazol-5-yl, isoxazol-4-yl, imidazol-5-yl, triazol-5-yl, tetrazol-5-yl, A more specific embodiment (G5) of embodiment G is a Compound of Formula I where $R^6$ is thien-2-yl, thien-3-yl, pyrrol-2-yl, furan-2-yl, furan-3-yl, pyrazol-3-yl, pyrazol-4-yl, pyrazol-5-yl, thiazol-2-yl, thiazol-5-yl, isoxazol-4-yl, imidazol-5-yl, triazol-5-yl, or tetrazol-5-yl, each of which is optionally substituted with one $R^9$ where $R^9$, when present, is methyl, benzyl, cyano, phenyl, N-tert-butoxycarbonyl, or chloro.

A more specific embodiment (G6) of embodiment G is a Compound of Formula I where $R^6$ is indolyl, benzimidazolyl, benzofuranyl, benzoxazolyl, or benzoisoxazolyl each of which is optionally substituted with 1, 2, 3, 4, or 5 $R^9$ groups. Specifically, $R^6$ is indol-2-yl, indol-3-yl, indol-4-yl, indol-5-yl, indol-6-yl, indol-7-yl, benzimidazol-2-yl, benzimidazol-4-yl, benzimidazol-5-yl, benzimidazol-6-yl, benzimidazol-7-yl, benzofuran-2-yl, benzofuran-3-yl, benzofuran-4-yl, benzofuran-5-yl, benzofuran-6-yl, benzofuran-7-yl, benzoxazol-2-yl, benzoxazol-4-yl, benzoxazol-5-yl, benzoxazol-6-yl, benzoxazol-7-yl, benzoisoxazol-3-yl, benzoisoxazol-4-yl, benzoisoxazol-5-yl, benzoisoxazol-6-yl, or benzoisoxazol-7-yl; each of which is optionally substituted with 1, 2, 3, 4, or 5 $R^9$ groups. More specifically, $R^6$ is indol-6-yl.

Another embodiment of the Invention (H) is a Compound of Formula I where $R^1$ is hydrogen, optionally substituted alkyl, optionally substituted cycloalkyl, optionally substituted heterocycloalkylalkyl, or optionally substituted arylalkyl; X is —NH—; $R^2$ is hydrogen or alkyl where the alkyl is optionally substituted with one or two $R^8$ groups; $R^4$ is alkyl; $R^5$ is hydrogen; $R^6$ is phenyl or heteroaryl wherein the phenyl and heteroaryl are optionally substituted with one, two, or three $R^9$ groups; each $R^8$, when present, is independently amino, alkylamino, dialkylamino, or halo; and each $R^9$, when present, is independently alkyl, arylalkyl, cyano, aryl, alkoxycarbonyl, or halo.

Another embodiment of the Invention (J) is a Compound of Formula I where $R^6$ is pyrazol-3-yl, pyrazol-4-yl, pyrazol-5-yl, imidazol-2-yl, imidazol-4-yl, imidazol-5-yl, thien-2-yl, thien-3-yl, thiazol-2-yl, thiazol-4-yl, thiazol-5-yl, oxazol-2-yl, oxazol-4-yl, oxazol-5-yl, isoxazol-3-yl, isoxazol-4-yl, isoxazol-5-yl, 1,2,3-oxadiazol-4-yl, 1,2,3-oxadiazol-5-yl, 1,3,4-oxadiazol-2-yl, 1,2,4-oxadiazol-3-yl, 1,2,4-oxadiazol- 5-yl, furan-2-yl, furan-3-yl, pyrrol-2-yl, pyrrol-3-yl, triazol-4-yl, triazol-5-yl, or tetrazol-5-yl; each of which is optionally substituted with 1, 2, 3, 4, or 5 $R^9$ groups.

Another embodiment (K) of the Invention is a Compound of Formula I where $R^1$ is alkyl or cycloalkyl; $R^4$ is methyl; and $R^6$ is heteroaryl optionally substituted with one or two $R^9$ groups. Specifically, each $R^9$, when present, is independently alkyl, arylalkyl, cyano, aryl, alkoxycarbonyl, or halo. Specifically, $R^6$ is pyrazol-3-yl, pyrazol-4-yl, pyrazol-5-yl, imidazol-2-yl, imidazol-4-yl, imidazol-5-yl, thien-2-yl, thien-3-yl, thiazol-2-yl, thiazol-4-yl, thiazol-5-yl, oxazol-2-yl, oxazol-4-yl, oxazol-5-yl, isoxazol-3-yl, isoxazol-4-yl, isoxazol-5-yl, 1,2,3-oxadiazol-4-yl, 1,2,3-oxadiazol-5-yl, 1,3,4-oxadiazol-2-yl, 1,2,4-oxadiazol-3-yl, 1,2,4-oxadiazol-5-yl, furan-2-yl, furan-3-yl, pyrrol-2-yl, pyrrol-3-yl, triazol-4-yl, triazol-5-yl, or tetrazol-5-yl; each of which is optionally substituted with one $R^9$ where $R^9$, when present, is methyl, benzyl, cyano, phenyl, or N-tert-butoxycarbonyl.

A more specific embodiment (K1) of embodiment K is a Compound of Formula I where $R^2$ is hydrogen.

A more specific embodiment (K2) of embodiment K is a Compound of Formula I where $R^2$ is methyl or ethyl.

Another embodiment (L) of the Invention is a Compound of Formula I where $R^1$ is alkyl or cycloalkyl; $R^4$ is methyl; and $R^6$ is phenyl optionally substituted with one or two $R^9$ groups. Specifically each $R^9$, when present, is independently halo, alkoxy, or haloalkyl.

Another embodiment (M) of the Invention is a Compound of Formula I where $R^1$ is alkyl or cycloalkyl; $R^4$ is methyl; and $R^2$ is hydrogen.

Another embodiment (N) of the Invention is a Compound of Formula I where $R^1$ is alkyl or cycloalkyl; $R^4$ is methyl; and $R^2$ is optionally substituted alkyl.

Representative Compounds

Representative compounds of Formula I are depicted below. The examples are merely illustrative and do not limit the scope of the invention in any way. Compounds of the invention are named according to systematic application of the nomenclature rules agreed upon by the International Union of Pure and Applied Chemistry (IUPAC), International Union of Biochemistry and Molecular Biology (IUBMB), and the Chemical Abstracts Service (CAS). Names were generated using ACD/Labs naming software 8.00 release, product version 8.08.

TABLE 1

| Example | Structure | Name |
|---|---|---|
| 1 | 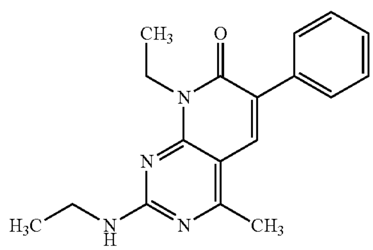 [SMILES: CCNc1nc(C)c2cc(-c3ccccc3)c(=O)n(CC)c2n1] | 8-ethyl-2-(ethylamino)-4-methyl-6-phenylpyrido[2,3-d]pyrimidin-7(8H)-one |
| 2 | 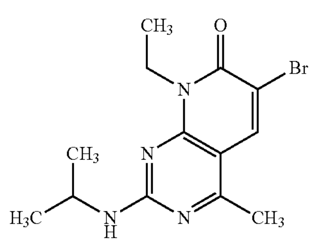 [SMILES: CCn1c(=O)c(Br)cc2c(C)nc(NC(C)C)nc21] | 6-bromo-8-ethyl-4-methyl-2-[(1-methylethyl)amino]pyrido[2,3-d]pyrimidin-7(8H)-one |
| 3 | 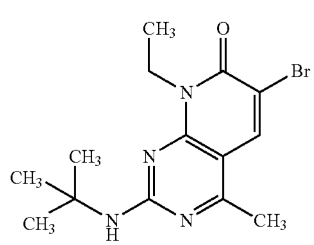 [SMILES: CCn1c(=O)c(Br)cc2c(C)nc(NC(C)(C)C)nc21] | 6-bromo-2-[(1,1-dimethylethyl)amino]-8-ethyl-4-methylpyrido[2,3-d]pyrimidin-7(8H)-one |

TABLE 1-continued

| Example | Structure | Name |
|---|---|---|
| 4 | 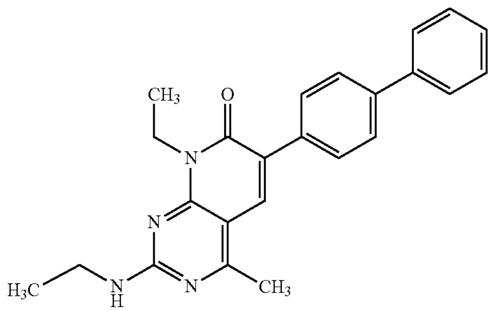 [SMILES: CCNc1nc(C)c2cc(-c3ccc(-c4ccccc4)cc3)c(=O)n(CC)c2n1] | 6-biphenyl-4-yl-8-ethyl-2-(ethylamino)-4-methylpyrido[2,3-d]pyrimidin-7(8H)-one |
| 5 | 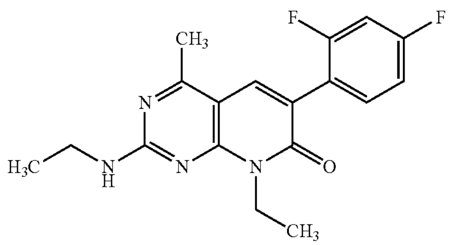 [SMILES: CCNc1nc(C)c2cc(-c3ccc(F)cc3F)c(=O)n(CC)c2n1] | 6-(2,4-difluorophenyl)-8-ethyl-2-(ethylamino)-4-methylpyrido[2,3-d]pyrimidin-7(8H)-one |
| 6 | 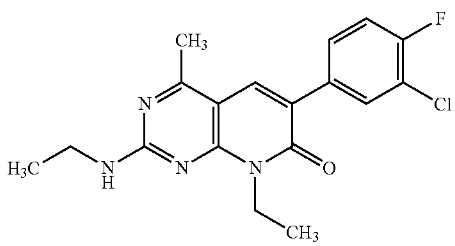 | 6-(3-chloro-4-fluorophenyl)-8-ethyl-2-(ethylamino)-4-methylpyrido[2,3-d]pyrimidin-7(8H)-one |
| 7 | 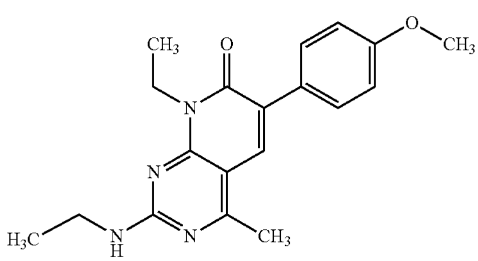 [SMILES: CCNc1nc(C)c2cc(-c3ccc(OC)cc3)c(=O)n(CC)c2n1] | 8-ethyl-2-(ethylamino)-4-methyl-6-[4-(methyloxy)phenyl]pyrido[2,3-d]pyrimidin-7(8H)-one |
| 8 | 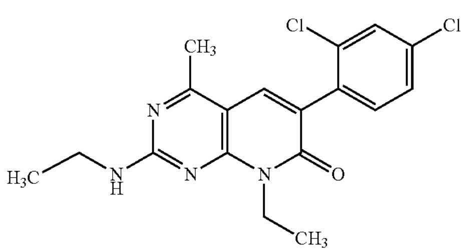 [SMILES: CCNc1nc(C)c2cc(-c3ccc(Cl)cc3Cl)c(=O)n(CC)c2n1] | 6-(2,4-dichlorophenyl)-8-ethyl-2-(ethylamino)-4-methylpyrido[2,3-d]pyrimidin-7(8H)-one |
| 9 | 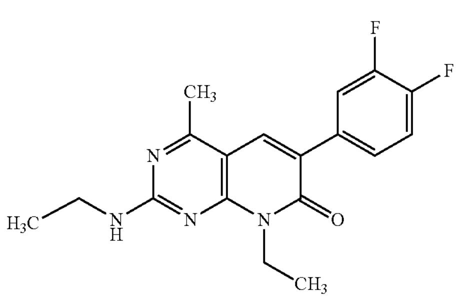 [SMILES: CCNc1nc(C)c2cc(-c3ccc(F)c(F)c3)c(=O)n(CC)c2n1] | 6-(3,4-difluorophenyl)-8-ethyl-2-(ethylamino)-4-methylpyrido[2,3-d]pyrimidin-7(8H)-one |

TABLE 1-continued

| Example | Structure | Name |
| --- | --- | --- |
| 10 | 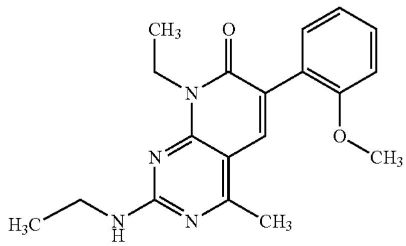 [SMILES: CCNc1nc(C)c2cc(-c3ccccc3OC)c(=O)n(CC)c2n1] | 8-ethyl-2-(ethylamino)-4-methyl-6-[2-(methyloxy)phenyl]pyrido[2,3-d]pyrimidin-7(8H)-one |
| 11 | 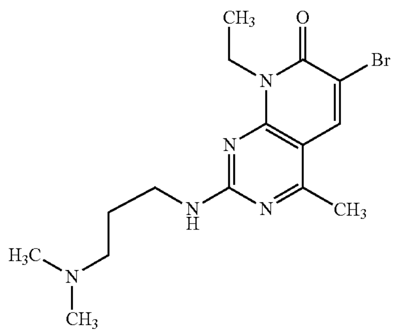 [SMILES: CCn1c(=O)c(Br)cc2c(C)nc(NCCCN(C)C)nc21] | 6-bromo-2-([3-(dimethylamino)propyl]amino)-8-ethyl-4-methylpyrido[2,3-d]pyrimidin-7(8H)-one |
| 12 | 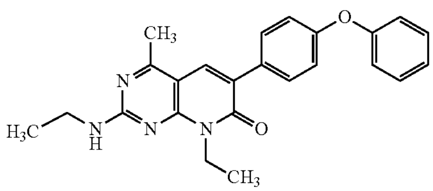 [SMILES: CCNc1nc(C)c2cc(-c3ccc(Oc4ccccc4)cc3)c(=O)n(CC)c2n1] | 8-ethyl-2-(ethylamino)-4-methyl-6-[4-(phenyloxy)phenyl]pyrido[2,3-d]pyrimidin-7(8H)-one |
| 13 | 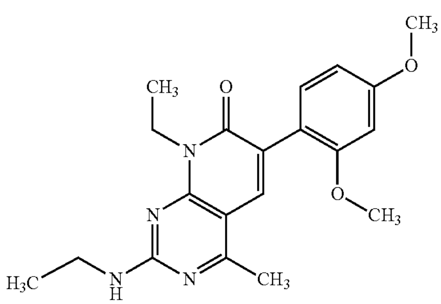 [SMILES: CCNc1nc(C)c2cc(-c3ccc(OC)cc3OC)c(=O)n(CC)c2n1] | 6-[2,4-bis(methyloxy)phenyl]-8-ethyl-2-(ethylamino)-4-methylpyrido[2,3-d]pyrimidin-7(8H)-one |
| 14 | 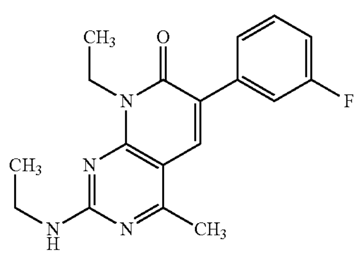 [SMILES: CCNc1nc(C)c2cc(-c3cccc(F)c3)c(=O)n(CC)c2n1] | 8-ethyl-2-(ethylamino)-6-(3-fluorophenyl)-4-methylpyrido[2,3-d]pyrimidin-7(8H)-one |
| 15 | 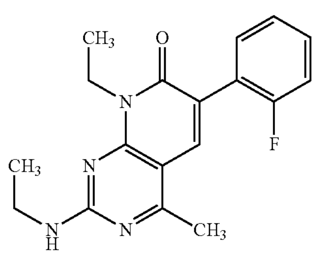 [SMILES: CCNc1nc(C)c2cc(-c3ccccc3F)c(=O)n(CC)c2n1] | 8-ethyl-2-(ethylamino)-6-(2-fluorophenyl)-4-methylpyrido[2,3-d]pyrimidin-7(8H)-one |

TABLE 1-continued

| Example | Structure | Name |
|---|---|---|
| 16 | 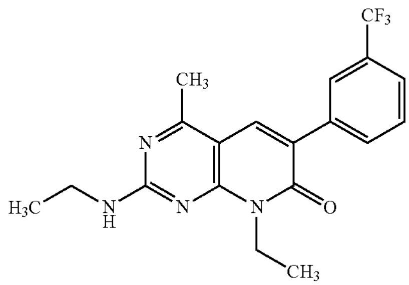 | 8-ethyl-2-(ethylamino)-4-methyl-6-[3-(trifluoromethyl)phenyl]pyrido[2,3-d]pyrimidin-7(8H)-one |
| 17 | 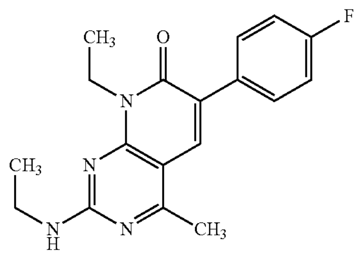 [SMILES: CCNc1nc(C)c2cc(-c3ccc(F)cc3)c(=O)n(CC)c2n1] | 8-ethyl-2-(ethylamino)-6-(4-fluorophenyl)-4-methylpyrido[2,3-d]pyrimidin-7(8H)-one |
| 18 | 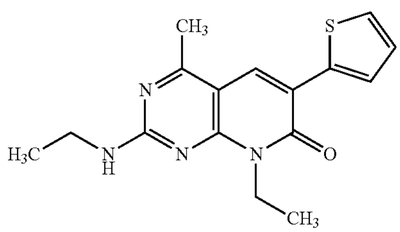 [SMILES: CCNc1nc(C)c2cc(-c3cccs3)c(=O)n(CC)c2n1] | 8-ethyl-2-(ethylamino)-4-methyl-6-(2-thienyl)pyrido[2,3-d]pyrimidin-7(8H)-one |
| 19 | 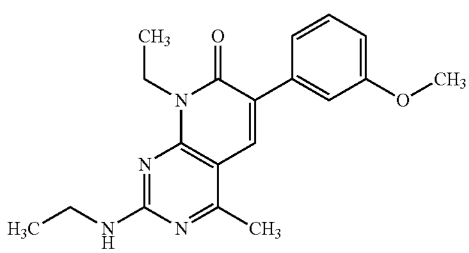 [SMILES: CCNc1nc(C)c2cc(-c3cccc(OC)c3)c(=O)n(CC)c2n1] | 8-ethyl-2-(ethylamino)-4-methyl-6-[3-(methyloxy)phenyl]pyrido[2,3-d]pyrimidin-7(8H)-one |
| 20 | 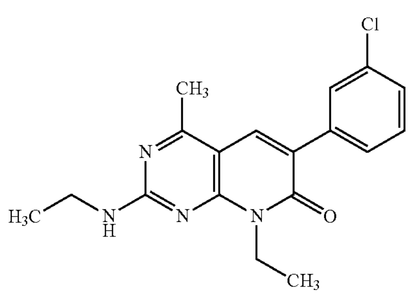 [SMILES: CCNc1nc(C)c2cc(-c3cccc(Cl)c3)c(=O)n(CC)c2n1] | 6-(3-ehlorophenyl)-8-ethyl-2-(ethylamino)-4-methylpyrido[2,3-d]pyrimidin-7(8H)-one |
| 21 | 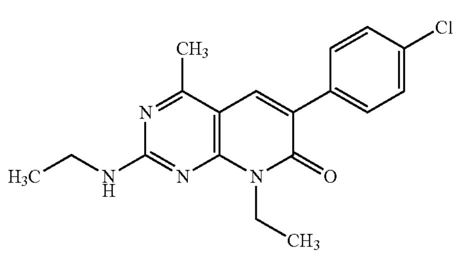 [SMILES: CCNc1nc(C)c2cc(-c3ccc(Cl)cc3)c(=O)n(CC)c2n1] | 6-(4-chlorophenyl)-8-ethyl-2-(ethylamino)-4-methylpyrido[2,3-d]pyrimidin-7(8H)-one |

TABLE 1-continued

| Example | Structure | Name |
|---|---|---|
| 22 | 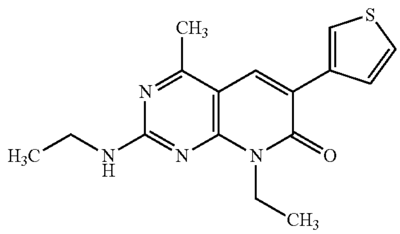 [SMILES: CCNc1nc(C)c2cc(-c3ccsc3)c(=O)n(CC)c2n1] | 8-ethyl-2-(ethylamino)-4-methyl-6-(3-thienyl)pyrido[2,3-d]pyrimidin-7(8H)-one |
| 23 | 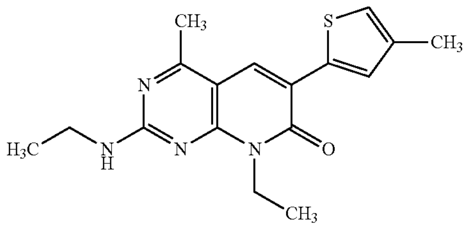 [SMILES: CCNc1nc(C)c2cc(-c3cc(C)cs3)c(=O)n(CC)c2n1] | 8-ethyl-2-(ethylamino)-4-methyl-6-(4-methyl-2-thienyl)pyrido[2,3-d]pyrimidin-7(8H)-one |
| 24 | 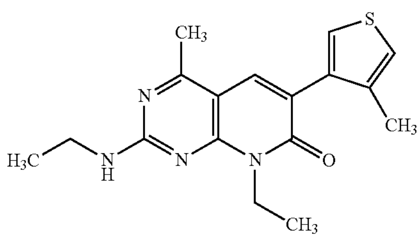 [SMILES: CCNc1nc(C)c2cc(-c3cscc3C)c(=O)n(CC)c2n1] | 8-ethyl-2-(ethylamino)-4-methyl-6-(4-methyl-3-thienyl)pyrido[2,3-d]pyrimidin-7(8H)-one |
| 25 | 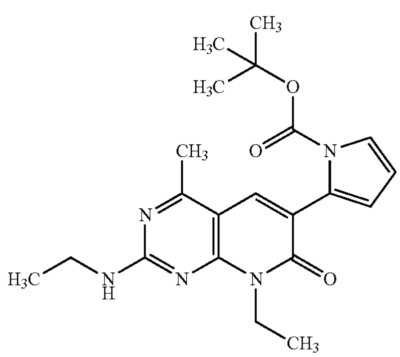 [SMILES: CCNc1nc(C)c2cc(-c3cccn3C(=O)OC(C)(C)C)c(=O)n(CC)c2n1] | 1,1-dimethylethyl 2-[8-ethyl-2-(ethylamino)-4-methyl-7-oxo-7,8-dihydropyrido[2,3-d]pyrimidin-6-yl]-1H-pyrrole-1-carboxylate |
| 26 | 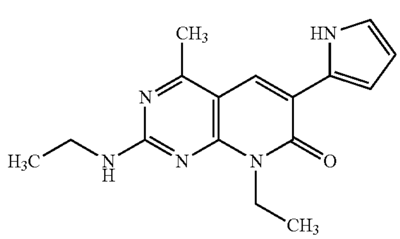 [SMILES: CCNc1nc(C)c2cc(-c3ccc[nH]3)c(=O)n(CC)c2n1] | 8-ethyl-2-(ethylamino)-4-methyl-6-(1H-pyrrol-2-yl)pyrido[2,3-d]pyrimidin-7(8H)-one |
| 27 | 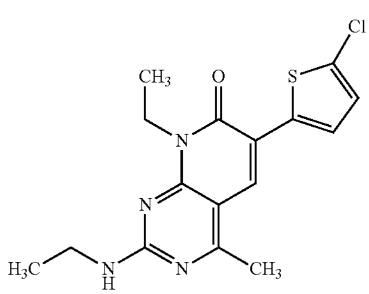 [SMILES: CCNc1nc(C)c2cc(-c3ccc(Cl)s3)c(=O)n(CC)c2n1] | 6-(5-chloro-2-thienyl)-8-ethyl-2-(ethylamino)-4-methylpyrido[2,3-d]pyrimidin-7(8H)-one |

TABLE 1-continued

| Example | Structure | Name |
|---|---|---|
| 28 | 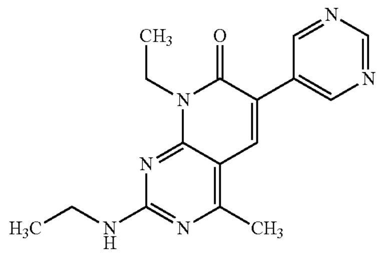 [SMILES: CCNc1nc(C)c2cc(-c3cncnc3)c(=O)n(CC)c2n1] | 8-ethyl-2-(ethylamino)-4-methyl-6-pyrimidin-5-ylpyrido[2,3-d]pyrimidin-7(8H)-one |
| 29 | 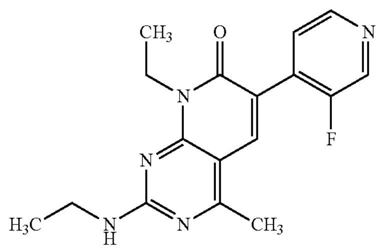 [SMILES: CCNc1nc(C)c2cc(-c3ccncc3F)c(=O)n(CC)c2n1] | 8-ethyl-2-(ethylamino)-6-(3-fluoropyridiN-4-yl)-4-methylpyrido[2,3-d]pyrimidin-7(8H)-one |
| 30 | 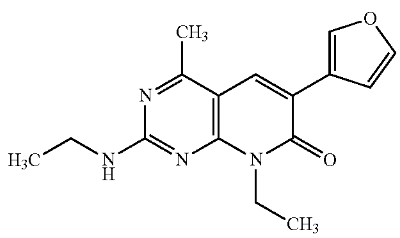 [SMILES: CCNc1nc(C)c2cc(-c3ccoc3)c(=O)n(CC)c2n1] | 8-ethyl-2-(ethylamino)-6-furan-3-yl-4-methylpyrido[2,3-d]pyrimidin-7(8H)-one |
| 31 | 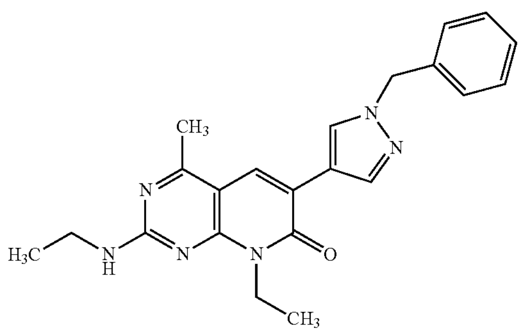 [SMILES: CCNc1nc(C)c2cc(-c3cnn(Cc4ccccc4)c3)c(=O)n(CC)c2n1] | 8-ethyl-2-(ethylamino)-4-methyl-6-[1-(phenylmethyl)-1H-pyrazol-4-yl]pyrido[2,3-d]pyrimidin-7(8H)-one |
| 32 | 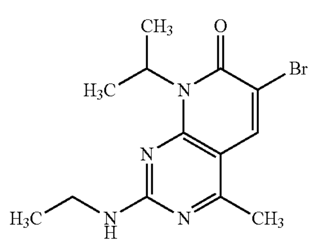 [SMILES: CCNc1nc(C)c2cc(Br)c(=O)n(C(C)C)c2n1] | 6-bromo-2-(ethylamino)-4-methyl-8-(1-methylethy)pyrido[2,3-d]pyrimidin-7(8H)-one |
| 33 | 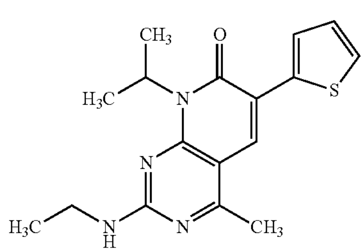 [SMILES: CCNc1nc(C)c2cc(-c3cccs3)c(=O)n(C(C)C)c2n1] | 2-(ethylamino)-4-methyl-8-(1-methylethyl)-6-(2-thienyl)pyrido[2,3-d]pyrimidin-7(8H)-one |

TABLE 1-continued

| Example | Structure | Name |
|---|---|---|
| 34 | 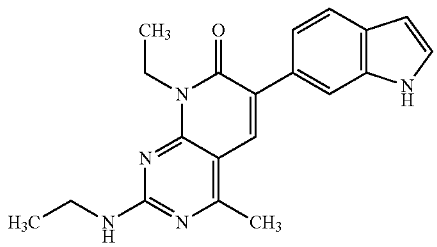 [SMILES: CCNc1nc(C)c2cc(-c3ccc4cc[nH]c4c3)c(=O)n(CC)c2n1] | 8-ethyl-2-(ethylamino)-6-(1H-indol-6-yl)-4-methylpyrido[2,3-d]pyrimidin-7(8H)-one |
| 35 | 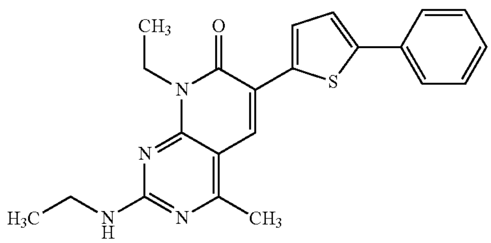 [SMILES: CCNc1nc(C)c2cc(-c3ccc(-c4ccccc4)s3)c(=O)n(CC)c2n1] | 8-ethyl-2-(ethylamino)-4-methyl-6-(5-phenyl-2-thienyl)pyrido[2,3-d]pyrimidin-7(8H)-one |
| 36 | 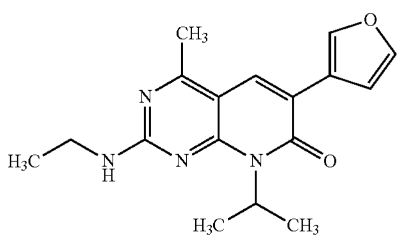 [SMILES: CCNc1nc(C)c2cc(-c3ccoc3)c(=O)n(C(C)C)c2n1] | 2-(ethylamino)-6-furan-3-yl-4-methyl-8-(1-methylethyl)pyrido[2,3-d]pyrimidin-7(8H)-one |
| 37 | 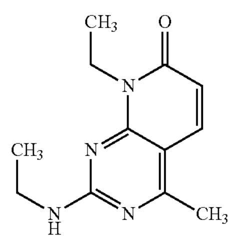 [SMILES: CCNc1nc(C)c2ccc(=O)n(CC)c2n1] | 8-ethyl-2-(ethylamino)-4-methylpyrido[2,3-d]pyrimidin-7(8H)-one |
| 38 | 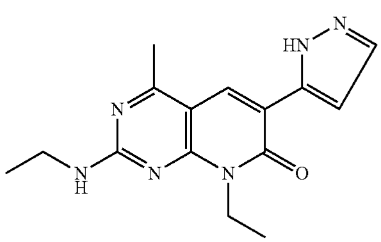 [SMILES: CCNc1nc(C)c2cc(-c3ccn[nH]3)c(=O)n(CC)c2n1] | 8-ethyl-2-(ethylamino)-4-methyl-6-(1H-pyrazol-5-yl)pyrido[2,3-d]pyrimidin-7(8H)-one |
| 39 | 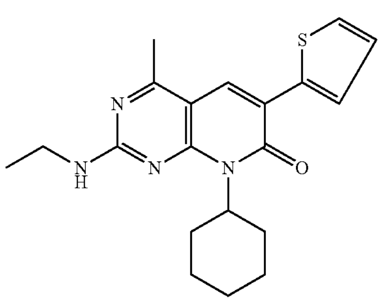 [SMILES: CCNc1nc(C)c2cc(-c3cccs3)c(=O)n(C3CCCCC3)c2n1] | 8-cyclohexyl-2-(ethylamino)-4-methyl-6-(2-thienyl)pyrido[2,3-d]pyrimidin-7(8H)-one |

TABLE 1-continued
| Example | Structure | Name |
|---|---|---|
| 40 | 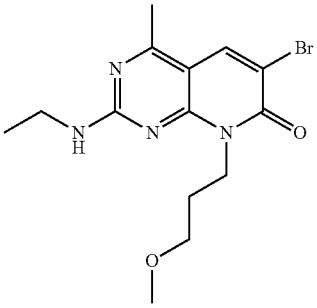 [SMILES: CCNc1nc(C)c2cc(Br)c(=O)n(CCCOC)c2n1] | 6-bromo-2-(ethylamino)-4-methyl-8-[3-(methyloxy)propyl]pyrido[2,3-d]pyrimidin-7(8H)-one |
| 41 | 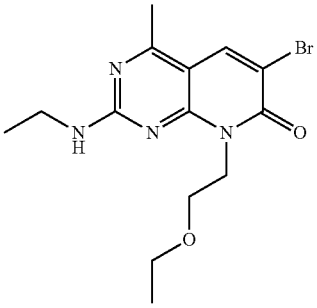 [SMILES: CCNc1nc(C)c2cc(Br)c(=O)n(CCOCC)c2n1] | 6-bromo-2-(ethylamino)-8-[2-(ethyloxy)ethyl]-4-methylpyrido[2,3-d]pyrimidin-7(8H)-one |
| 42 | 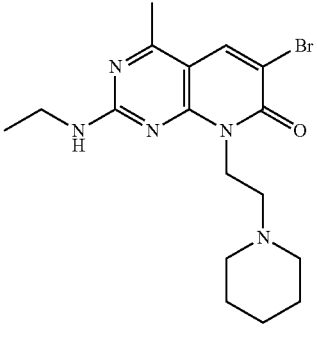 [SMILES: CCNc1nc(C)c2cc(Br)c(=O)n(CCN3CCCCC3)c2n1] | 6-bromo-2-(ethylamino)-4-methyl-8-(2-piperidin-1-ylethyl)pyrido[2,3-d]pyrimidin-7(8H)-one |
| 43 | 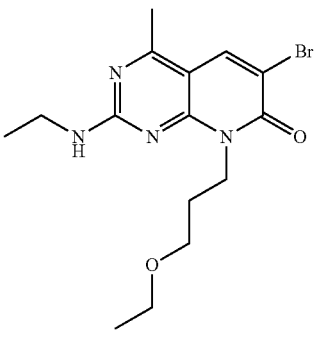 [SMILES: CCNc1nc(C)c2cc(Br)c(=O)n(CCCOCC)c2n1] | 6-bromo-2-(ethylamino)-8-[3-(ethyloxy)propyl]-4-methylpyrido[2,3-d]pyrimidin-7(8H)-one |

TABLE 1-continued

| Example | Structure | Name |
|---|---|---|
| 44 | 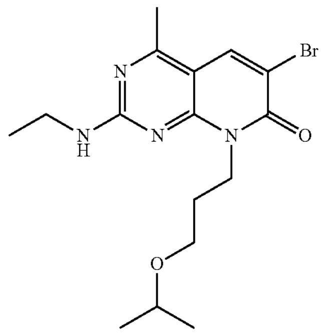 [SMILES: CCNc1nc(C)c2cc(Br)c(=O)n(CCCOC(C)C)c2n1] | 6-bromo-2-(ethylamino)-4-methyl-8-(3-[(1-methylethyl)oxy]propyl)pyrido[2,3-d]pyrimidin-7(8H)-one |
| 45 | 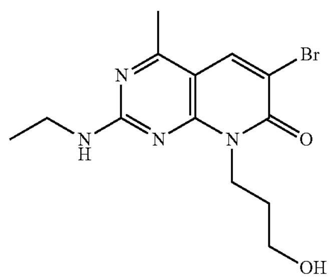 [SMILES: CCNc1nc(C)c2cc(Br)c(=O)n(CCCO)c2n1] | 6-bromo-2-(ethylamino)-8-(3-hydroxypropyl)-4-methylpyrido[2,3-d]pyrimidin-7(8H)-one |
| 46 | 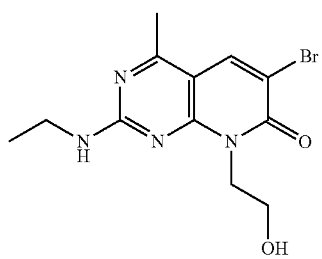 [SMILES: CCNc1nc(C)c2cc(Br)c(=O)n(CCO)c2n1] | 6-bromo-2-(ethylamino)-8-(2-hydroxyethyl)-4-methylpyrido[2,3-d]pyrimidin-7(8H)-one |
| 47 | 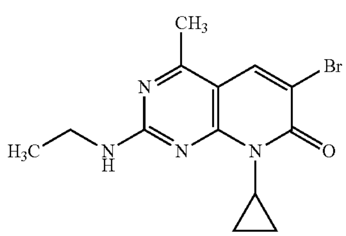 [SMILES: CCNc1nc(C)c2cc(Br)c(=O)n(C3CC3)c2n1] | 6-bromo-8-cyclopropyl-2-(ethylamino)-4-methylpyrido[2,3-d]pyrimidin-7(8H)-one |
| 48 | 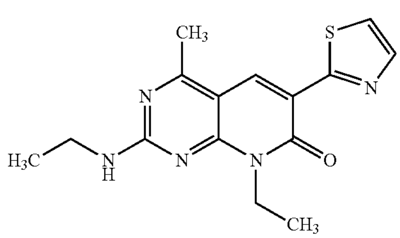 [SMILES: CCNc1nc(C)c2cc(-c3nccs3)c(=O)n(CC)c2n1] | 8-ethyl-2-(ethylamino)-4-methyl-6-(1,3-thiazol-2-yl)pyrido[2,3-d]pyrimidin-7(8H)-one |
| 49 | 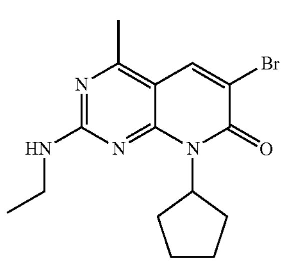 [SMILES: CCNc1nc(C)c2cc(Br)c(=O)n(C3CCCC3)c2n1] | 6-bromo-8-cyclopentyl-2-(ethylamino)-4-methylpyrido[2,3-d]pyrimidin-7(8H)-one |

TABLE 1-continued

| Example | Structure | Name |
|---|---|---|
| 50 | 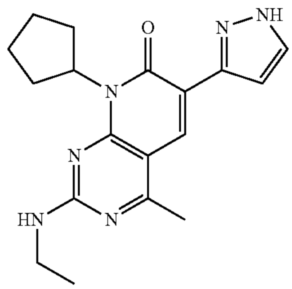 [SMILES: CCNc1nc(C)c2cc(-c3cc[nH]n3)c(=O)n(C3CCCC3)c2n1] | 8-cyclopentyl-2-(ethylamino)-4-methyl-6-(1H-pyrazol-3-yl)pyrido[2,3-d]pyrimidin-7(8H)-one |
| 51 | 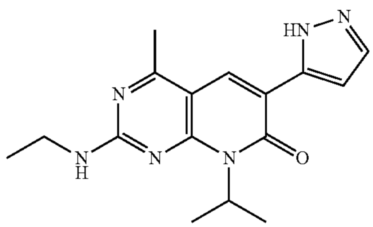 [SMILES: CCNc1nc(C)c2cc(-c3ccn[nH]3)c(=O)n(C(C)C)c2n1] | 2-(ethylamino)-4-methyl-8-(1-methylethyl)-6-(1H-pyrazol-5-yl)pyrido[2,3-d]pyrimidin-7(8H)-one |
| 52 | 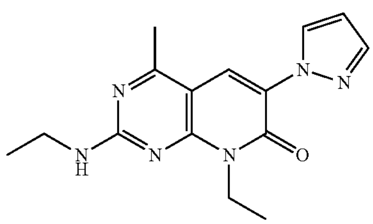 [SMILES: CCNc1nc(C)c2cc(-n3cccn3)c(=O)n(CC)c2n1] | 8-ethyl-2-(ethylamino)-4-methyl-6-(1H-pyrazol-1-yl)pyrido[2,3-d]pyrimidin-7(8H)-one |
| 53 | 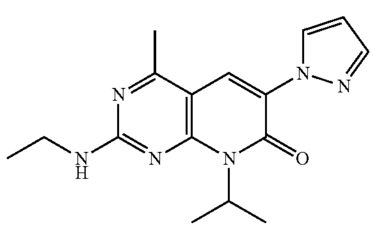 [SMILES: CCNc1nc(C)c2cc(-n3cccn3)c(=O)n(C(C)C)c2n1] | 2-(ethylamino)-4-methyl-8-(1-methylethyl)-6-(1H-pyrazol-1-yl)pyrido[2,3-d]pyrimidin-7(8H)-one |
| 54 | 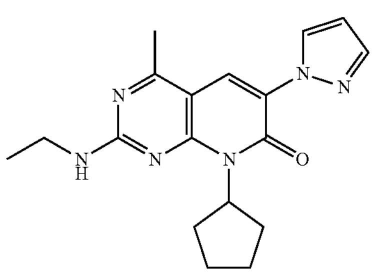 [SMILES: CCNc1nc(C)c2cc(-n3cccn3)c(=O)n(C3CCCC3)c2n1] | 8-cyclopentyl-2-(ethylamino)-4-methyl-6-(1H-pyrazol-1-yl)pyrido[2,3-d]pyrimidin-7(8H)-one |
| 55 | 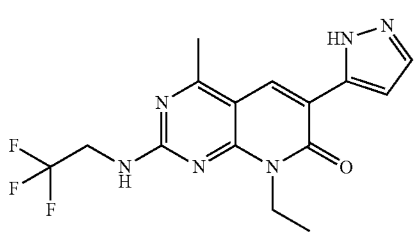 [SMILES: CCn1c(=O)c(-c2ccn[nH]2)cc2c(C)nc(NCC(F)(F)F)nc21] | 8-ethyl-4-methyl-6-(1H-pyrazol-5-yl)-2-[(2,2,2-trifluoroethyl)amino]pyrido[2,3-d]pyrimidin-7(8H)-one |

TABLE 1-continued

| Example | Structure | Name |
|---|---|---|
| 56 | 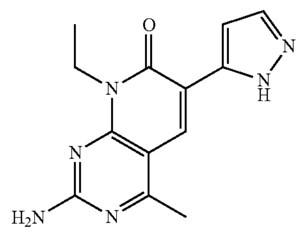 [SMILES: CCn1c(=O)c(-c2ccn[nH]2)cc2c(C)nc(N)nc21] | 2-amino-8-ethyl-4-methyl-6-(1H-pyrazol-5-yl)pyrido[2,3-d]pyrimidin-7(8H)-one |
| 57 | 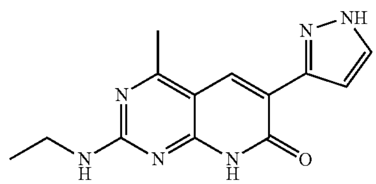 [SMILES: CCNc1nc(C)c2cc(-c3cc[nH]n3)c(=O)[nH]c2n1] | 2-(ethylamino)-4-methyl-6-(1H-pyrazol-3-yl)pyrido[2,3-d]pyrimidin-7(8H)-one |
| 58 | 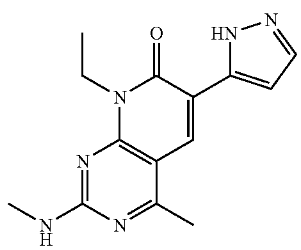 [SMILES: CCn1c(=O)c(-c2ccn[nH]2)cc2c(C)nc(NC)nc21] | 8-ethyl-4-methyl-2-(methylamino)-6-(1H-pyrazol-5-yl)pyrido[2,3-d]pyrimidin-7(8H)-one |
| 59 | 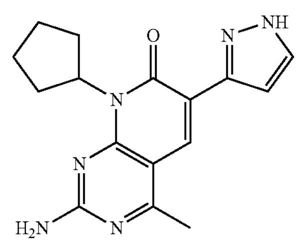 [SMILES: Cc1nc(N)nc2c1cc(-c1cc[nH]n1)c(=O)n2C1CCCC1] | 2-amino-8-cyclopentyl-4-methyl-6-(1H-pyrazol-3-yl)pyrido[2,3-d]pyrimidin-7(8H)-one |
| 60 | 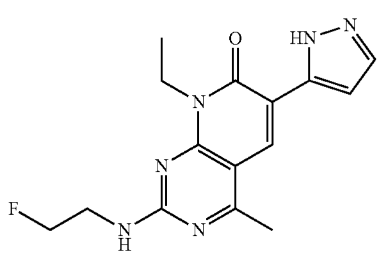 [SMILES: CCn1c(=O)c(-c2ccn[nH]2)cc2c(C)nc(NCCF)nc21] | 8-ethyl-2-[(2-fluoroethyl)amino]-4-methyl-6-(1H-pyrazol-5-yl)pyrido[2,3-d]pyrimidin-7(8H)-one |
| 61 | 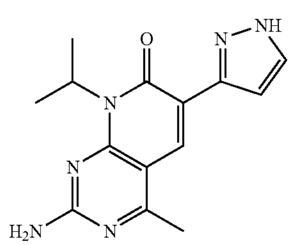 [SMILES: Cc1nc(N)nc2c1cc(-c1cc[nH]n1)c(=O)n2C(C)C] | 2-amino-4-methyl-8-(1-methylethyl)-6-(1H-pyrazol-3-yl)pyrido[2,3-d]pyrimidin-7(8H)-one |

TABLE 1-continued

| Example | Structure | Name |
|---|---|---|
| 62 | 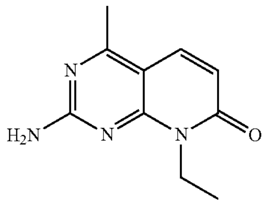 | 2-amino-8-ethyl-4-methylpyrido[2,3-d]pyrimidin-7(8H)-one |
| 63 | 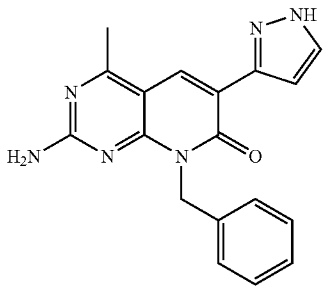 [SMILES: Cc1nc(N)nc2c1cc(-c1cc[nH]n1)c(=O)n2Cc1ccccc1] | 2-amino-4-methyl-8-(phenylmethyl)-6-(1H-pyrazol-3-yl)pyrido[2,3-d]pyrimidin-7(8H)-one |
| 64 | 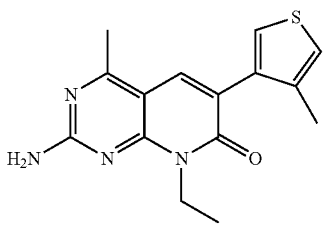 [SMILES: CCn1c(=O)c(-c2cscc2C)cc2c(C)nc(N)nc21] | 2-amino-8-ethyl-4-methyl-6-(4-methyl-3-thienyl)pyrido[2,3-d]pyrimidin-7(8H)-one |
| 65 | 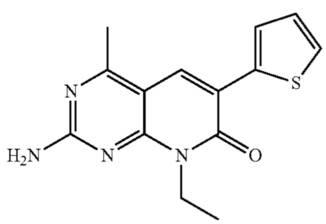 [SMILES: CCn1c(=O)c(-c2cccs2)cc2c(C)nc(N)nc21] | 2-amino-8-ethyl-4-methyl-6-(2-thienyl)pyrido[2,3-d]pyrimidin-7(8H)-one |
| 66 | 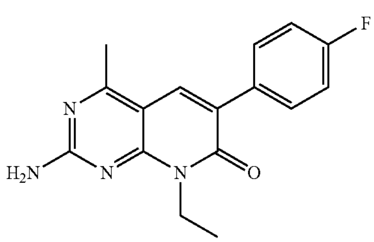 [SMILES: CCn1c(=O)c(-c2ccc(F)cc2)cc2c(C)nc(N)nc21] | 2-amino-8-ethyl-6-(4-fluorophenyl)-4-methylpyrido[2,3-d]pyrimidin-7(8H)-one |
| 67 | 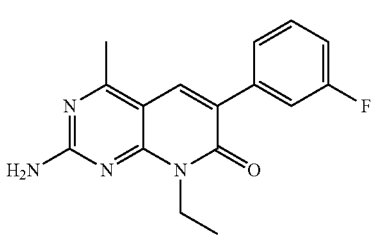 [SMILES: CCn1c(=O)c(-c2cccc(F)c2)cc2c(C)nc(N)nc21] | 2-amino-8-ethyl-6-(3-fluorophenyl)-4-methylpyrido[2,3-d]pyrimidin-7(8H)-one |

TABLE 1-continued

| Example | Structure | Name |
|---|---|---|
| 68 | 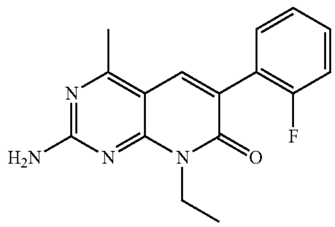 [SMILES: CCn1c(=O)c(-c2ccccc2F)cc2c(C)nc(N)nc21] | 2-amino-8-ethyl-6-(2-fluorophenyl)-4-methylpyrido[2,3-d]pyrimidin-7(8H)-one |
| 69 | 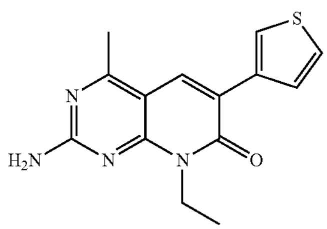 [SMILES: CCn1c(=O)c(-c2ccsc2)cc2c(C)nc(N)nc21] | 2-amino-8-ethyl-4-methyl-6-(3-thienyl)pyrido[2,3-d]pyrimidin-7(8H)-one |
| 70 | 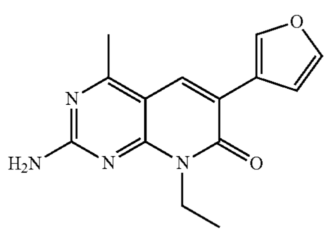 [SMILES: CCn1c(=O)c(-c2ccoc2)cc2c(C)nc(N)nc21] | 2-amino-8-ethyl-6-furan-3-yl-4-methylpyrido[2,3-d]pyrimidin-7(8H)-one |
| 71 | 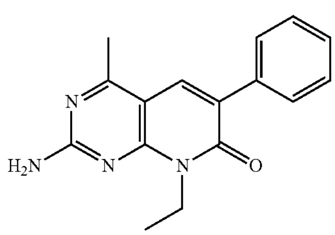 [SMILES: CCn1c(=O)c(-c2ccccc2)cc2c(C)nc(N)nc21] | 2-amino-8-ethyl-4-methyl-6-phenylpyrido[2,3-d]pyrimidin-7(8H)-one |
| 72 | 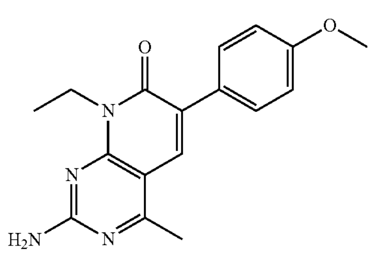 [SMILES: CCn1c(=O)c(-c2ccc(OC)cc2)cc2c(C)nc(N)nc21] | 2-amino-8-ethyl-4-methyl-6-[4-(methyloxy)phenyl]pyrido[2,3-d]pyrimidin-7(8H)-one |
| 73 | 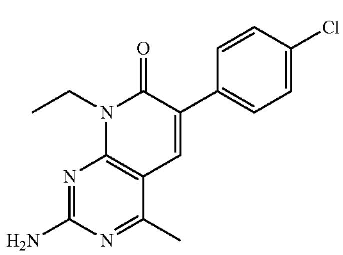 [SMILES: CCn1c(=O)c(-c2ccc(Cl)cc2)cc2c(C)nc(N)nc21] | 2-amino-6-(4-chlorophenyl)-8-ethyl-4-methylpyrido[2,3-d]pyrimidin-7(8H)-one |

TABLE 1-continued

| Example | Structure | Name |
|---|---|---|
| 74 | 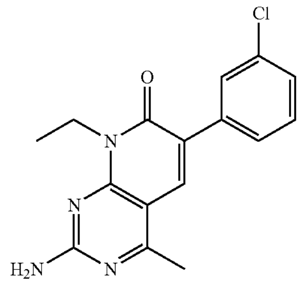 [SMILES: CCn1c(=O)c(-c2cccc(Cl)c2)cc2c(C)nc(N)nc21] | 2-amino-6-(3-chlorophenyl)-8-ethyl-4-methylpyrido[2,3-d]pyrimidin-7(8H)-one |
| 75 | 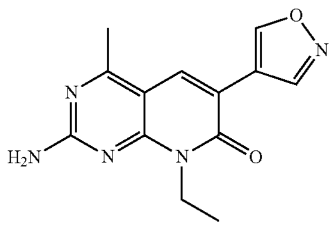 [SMILES: CCn1c(=O)c(-c2cnoc2)cc2c(C)nc(N)nc21] | 2-amino-8-ethyl-6-isoxazol-4-yl-4-methylpyrido[2,3-d]pyrimidin-7(8H)-one |
| 76 | 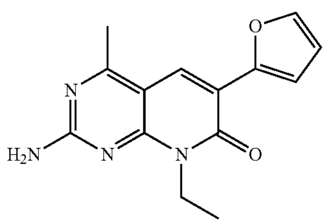 [SMILES: CCn1c(=O)c(-c2ccco2)cc2c(C)nc(N)nc21] | 2-amino-8-ethyl-6-furan-2-yl-4-methylpyrido[2,3-d]pyrimidin-7(8H)-one |
| 77 | 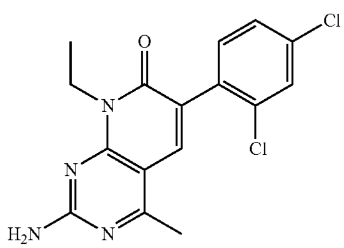 [SMILES: CCn1c(=O)c(-c2ccc(Cl)cc2Cl)cc2c(C)nc(N)nc21] | 2-amino-6-(2,4-dichlorophenyl)-8-ethyl-4-methylpyrido[2,3-d]pyrimidin-7(8H)-one |
| 78 | 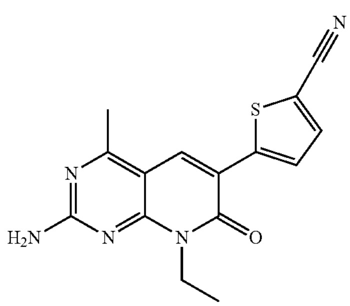 [SMILES: CCn1c(=O)c(-c2ccc(C#N)s2)cc2c(C)nc(N)nc21] | 5-(2-amino-8-ethyl-4-methyl-7-oxo-7,8-dihydropyrido[2,3-d]pyrimidin-6-yl)thiophene-2-carbonitrile |
| 79 | 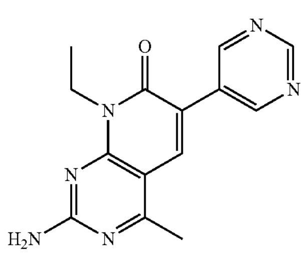 [SMILES: CCn1c(=O)c(-c2cncnc2)cc2c(C)nc(N)nc21] | 2-amino-8-ethyl-4-methyl-6-pyrimidin-5-ylpyrido[2,3-d]pyrimidin-7(8H)-one |

TABLE 1-continued

| Example | Structure | Name |
|---|---|---|
| 80 | 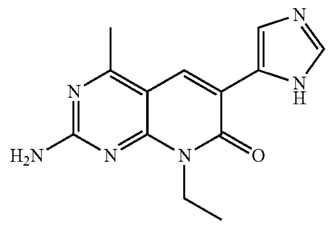 [SMILES: CCn1c(=O)c(-c2cnc[nH]2)cc2c(C)nc(N)nc21] | 2-amino-8-ethyl-6-(1H-imidazol-5-yl)-4-methylpyrido[2,3-d]pyrimidin-7(8H)-one |
| 81 | 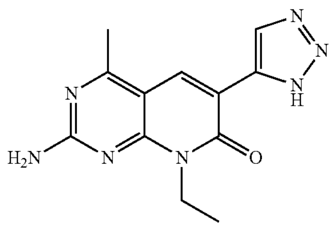 [SMILES: CCn1c(=O)c(-c2cnn[nH]2)cc2c(C)nc(N)nc21] | 2-amino-8-ethyl-4-methyl-6-(1H-1,2,3-triazol-5-yl)pyrido[2,3-d]pyrimidin-7(8H)-one |
| 82 | 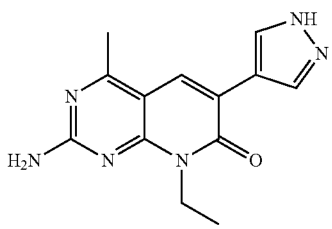 [SMILES: CCn1c(=O)c(-c2cn[nH]c2)cc2c(C)nc(N)nc21] | 2-amino-8-ethyl-4-methyl-6-(1H-pyrazol-4-yl)pyrido[2,3-d]pyrimidin-7(8H)-one |
| 83 | 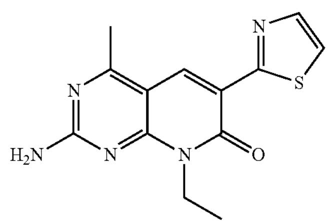 [SMILES: CCn1c(=O)c(-c2nccs2)cc2c(C)nc(N)nc21] | 2-amino-8-ethyl-4-methyl-6-(1,3-thiazol-2-yl)pyrido[2,3-d]pyrimidin-7(8H)-one |
| 84 | 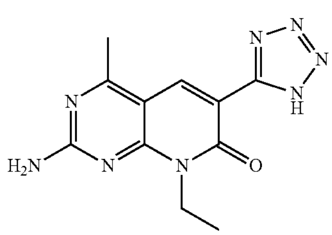 [SMILES: CCn1c(=O)c(-c2nnn[nH]2)cc2c(C)nc(N)nc21] | 2-amino-8-ethyl-4-methyl-6-(1H-tetrazol-5-yl)pyrido[2,3-d]pyrimidin-7(8H)-one |
| 85 | 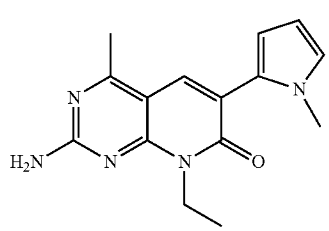 [SMILES: CCn1c(=O)c(-c2cccn2C)cc2c(C)nc(N)nc21] | 2-amino-8-ethyl-4-methyl-6-(1-methyl-1H-pyrrol-2-yl)pyrido[2,3-d]pyrimidin-7(8H)-one |

TABLE 1-continued

| Example | Structure | Name |
|---|---|---|
| 86 | 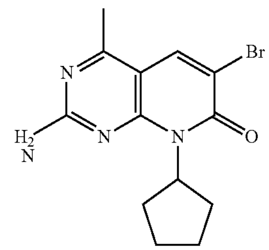 [SMILES: Cc1nc(N)nc2c1cc(Br)c(=O)n2C1CCCC1] | 2-amino-6-bromo-8-cyclopentyl-4-methylpyrido[2,3-d]pyrimidin-7(8H)-one |
| 87 | 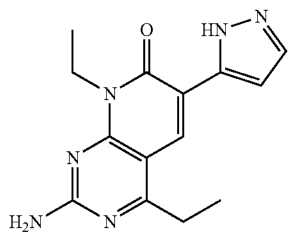 [SMILES: CCc1nc(N)nc2c1cc(-c1ccn[nH]1)c(=O)n2CC] | 2-amino-4,8-diethyl-6-(1H-pyrazol-5-yl)pyrido[2,3-d]pyrimidin-7(8H)-one |
| 88 | 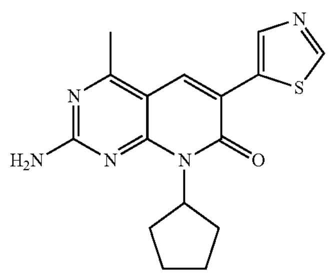 [SMILES: Cc1nc(N)nc2c1cc(-c1cncs1)c(=O)n2C1CCCC1] | 2-amino-8-cyclopentyl-4-methyl-6-(1,3-thiazol-5-yl)pyrido[2,3-d]pyrimidin-7(8H)-one |

General Administration

In one aspect, the invention provides pharmaceutical compositions comprising an inhibitor of the PI3Ks and mTOR of Formula I, optionally in combination with an autophagy inhibitor as described herein, and a pharmaceutically acceptable carrier, excipient, or diluent. In certain other specific embodiments, administration is by the oral route. Administration of the compounds of Formula I, or their pharmaceutically acceptable salts, in pure form or in an appropriate pharmaceutical composition in combination with an autophagy inhibitor as described herein, can be carried out via any of the accepted modes of administration or agents for serving similar utilities. Thus, the Compound of Formula I and the autophagy inhibitor can be administered in the same or separate vehicles. Administration can be, for example, orally, nasally, parenterally (intravenous, intramuscular, or subcutaneous), topically, transdermally, intravaginally, intravesically, intracisternally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, specifically in unit dosage forms suitable for simple administration of precise dosages.

The compositions will include a conventional pharmaceutical carrier or excipient and a Compound of Formula I as the/an active agent, optionally an autophagy inhibitor, and, in addition, may include carriers and adjuvants, and so on.

Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylalted hydroxytoluene, etc.

The choice of formulation depends on various factors such as the mode of drug administration (e.g., for oral administration, formulations in the form of tablets, pills or capsules) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a cross-linked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One specific route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Compressed gases may be used to disperse a compound of this invention in aerosol form. Inert gases suitable for this purpose are nitrogen, carbon dioxide, etc.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

In the pharmaceutical compositions disclosed herein, the compounds of Formula I, or their pharmaceutically acceptable salts or solvates, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of Formula I can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

If formulated as a fixed dose, such combination products employ the compounds of this invention within the dosage range described above and the other pharmaceutically active agent(s) within approved dosage ranges. Compounds of Formula I may alternatively be used sequentially with known pharmaceutically acceptable agent(s) when a combination formulation is inappropriate.

General Synthesis

Compounds of this invention can be made by the synthetic procedures described below. The starting materials and reagents used in preparing these compounds are either available from commercial suppliers such as Aldrich Chemical Co. (Milwaukee, Wis.), or Bachem (Torrance, Calif.), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4$^{th}$ Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure. The starting materials and the intermediates of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure and over a temperature range from about −78° C. to about 150° C., more specifically from about 0° C. to about 125° C. and more specifically at about room (or ambient) temperature, e.g., about 20° C. Unless otherwise stated (as in the case of an hydrogenation), all reactions are performed under an atmosphere of nitrogen.

Prodrugs can be prepared by techniques known to one skilled in the art. These techniques generally modify appropriate functional groups in a given compound. These modified functional groups regenerate original functional groups by routine manipulation or in vivo. Amides and esters of the compounds of the present invention may be prepared according to conventional methods. A thorough discussion of prodrugs is provided in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

The compounds of the invention, or their pharmaceutically acceptable salts, may have asymmetric carbon atoms or quaternized nitrogen atoms in their structure. Compounds of Formula I that may be prepared through the syntheses described herein may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of this invention. Some of the compounds of the invention may exist as tautomers. For example, where a ketone or aldehyde is present, the molecule may exist in the enol form; where an amide is present, the molecule may exist as the imidic acid; and where an enamine is present, the molecule may exist as an imine. All such tautomers are within the scope of the invention. In particular, imidazol-5-yl and pyrazol-5-yl each can also exist in their respective tautomeric forms imidazol-4-yl and pyrazol-3-yl. Regardless of which structure or which terminology is used, each tautomer is included within the scope of the Invention.

The present invention also includes N-oxide derivatives and protected derivatives of compounds of Formula I. For example, when compounds of Formula I contain an oxidizable nitrogen atom, the nitrogen atom can be converted to an N-oxide by methods well known in the art. When compounds of Formula I contain groups such as hydroxy, carboxy, thiol or any group containing a nitrogen atom(s), these groups can be protected with a suitable "protecting group" or "protective group". A comprehensive list of suitable protective groups can be found in T. W. Greene, *Protective Groups in Organic Synthesis*, John Wiley & Sons, Inc. 1991, the disclosure of which is incorporated herein by reference in its entirety. The protected derivatives of compounds of Formula I can be prepared by methods well known in the art.

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. Enantiomers (R- and S-isomers) may be resolved by methods known to one of ordinary skill in the art, for example by: formation of diastereoisomeric salts or complexes which may be separated, for example, by crystallization; via formation of diastereoisomeric derivatives which may be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents or by converting on enantiomer to the other by asymmetric transformation. For a mixture of enantiomers, enriched in a particular enantiomer, the major component enantiomer may be further enriched (with concomitant loss in yield) by recrystallization.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The chemistry for the preparation of the compounds of this invention is known to those skilled in the art. In fact, there may be more than one process to prepare the compounds of the invention. For specific examples, see M. Barvian et al. J. Med. Chem. 2000, 43, 4606-4616; S. N. VanderWei et al. J. Med. Chem. 2005, 48, 2371-2387; P. L. Toogood et al. J. Med. Chem. 2005, 48, 2388-2406; J. Kasparec et al. Tetrahedron Letters 2003, 44, 4567-4570; and references cited therein. See also U.S. Pre-grant publication US2004/0009993 A1 (M. Angiolini et al.), which is incorporated herein by reference, and references cited therein. The following examples illustrate but do not limit the invention. All references cited herein are incorporated by reference in their entirety.

A compound of the invention where $R^1$ is optionally substituted alkyl, $R^2$ is hydrogen or optionally substituted alkyl, $R^4$ is methyl or ethyl, $R^6$ is phenyl or heteroaryl each of which is optionally substituted with 1, 2, 3, 4, or 5 $R^9$ groups (as defined in the Summary of the Invention), and $R^2$ is hydrogen can be prepared according to Scheme 1.

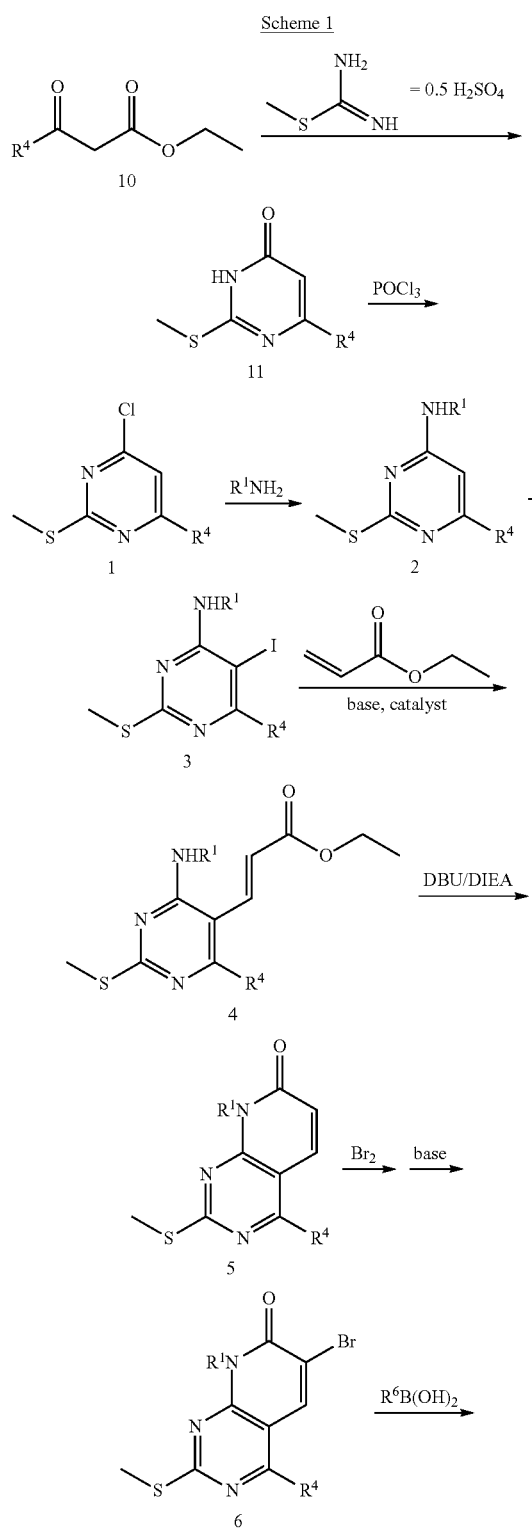

To a solution of commercially available 2-methyl-2-thiopseudourea sulfate in a solvent such as water is added a base such as sodium carbonate and an intermediate of formula 10 at room temperature. The reaction mixture is stirred for overnight or less. After neutralizing, 11 is collected through filtration and followed by drying under vacuum. 11 is then treated with POCl$_3$ and the reaction is heated to reflux for approximately 2 h and then concentrated under vacuum to dryness. 1 can be used directly in the next reaction without further purification.

An intermediate of formula 2 is prepared by reacting an intermediate of formula 1 with a primary amine $R^1NH_2$ in a solvent such as water and with heating. 2 is then treated with iodine monochloride in a solvent such as methanol at around 0° C. and allowed to react for approximately overnight or less as needed for the reaction to go to completion to form 3. After completion the residue is triturated with acetone. The intermediate 3 is then reacted in a solvent, such as DMA, with ethyl acrylate in the presence of a base, such as triethylamine, and in the presence of a catalyst, such as Pd(OAc)$_2$, and (+)BINAP. The reaction is heated to approximately 100° C. and allowed to react for approximately overnight or less as needed for the reaction to go to completion to form 4. 4 is then optionally purified by column chromatography.

5 is prepared by treating 4 with DBU in the presence of a base such as DIPEA at room temperature. The reaction mixture is then heated to reflux and reacted for approximately 15 h. After evaporation of solvent, the residue is triturated with acetone and collected by filtration to yield 5.

6 is prepared by reacting 5 with a brominating agent such as Br$_2$ in a solvent such as DCM at room temperature. The reaction mixture is then stirred for approximately overnight. The resulting product is filtered and then suspended in a solvent such as DCM and treated with a base such as triethylamine. The mixture is then washed with water and dried over a drying agent such as Na$_2$SO$_4$ to yield 6.

A Suzuki coupling is then performed using 6 and a boronic acid (or ester) of formula $R^6B(OH)_2$ in a solvent(s) such as a DME-H$_2$O mixture in the presence of a catalyst such as Pd(dpppf) and a base such as triethylamine at room temperature. The reaction mixture is heated to reflux for approximately 4 h. After cooling to room temperature, the reaction mixture is partitioned with water and ethyl acetate. After separation, the organic layer is dried over a drying agent such as Na$_2$SO$_4$ to yield 7.

The methylthio group of 7 is then oxidized with m-CPBA in a solvent such as DCM at room temperature allowing to stir for approximately 4 h. After removal of the solvent under reduced pressure, the product is treated with an amine of formula $R^2NH_2$ in a solvent such as dioxane and stirred at room temperature for approximately overnight to yield a Compound of Formula I.

Alternatively, a Compound of Formula I where $R^1$ is optionally substituted alkyl, $R^4$ is methyl or ethyl, $R^6$ is phenyl or heteroaryl each of which is optionally substituted with 1, 2, 3, 4, or 5 $R^9$ groups (as defined in the Summary of the Invention), and $R^2$ is hydrogen can be prepared according to Scheme 2.

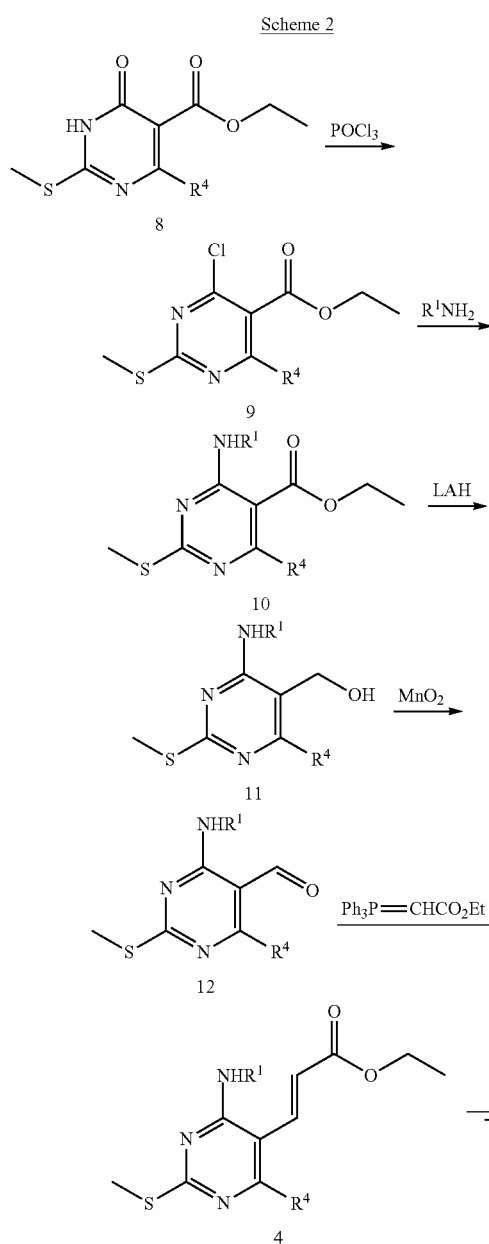

An intermediate of formula 9 is prepared by reacting an intermediate of formula 8 with neat $POCl_3$ and heating. 9 is then treated with a primary amine $R^1NH_2$ in a solvent such as water or THF and triethylamine at 0° C. to form 10. After removal of the solvent under reduced pressure, the intermediate 10 is then reacted with lithium aluminum hydride in a solvent such as TI-IF at 0° C. After quenching and aqueous workup, solvent removal provided crystalline 11 without further purification. Treatment of 11 with manganese (II) dioxide in a solvent such as methylene chloride or chloroform at room temperature provided aldehyde 12 upon filtration and solvent removal. A Wittig reaction with aldehyde 12 can be employed with (carbethoxymethylene)triphenylphosphorane in refluxing THF to provides the common intermediate 4. 4 can then be used to prepare a Compound of Formula I using the procedures described in Scheme 1.

A compound of the invention where $R^1$ is optionally substituted alkyl, $R^4$ is methyl or ethyl, $R^6$ is phenyl or heteroaryl each of which is optionally substituted with 1, 2, 3, 4, or 5 $R^9$ groups (as defined in the Summary of the Invention), and $R^2$ is hydrogen can be prepared according to Scheme 3.

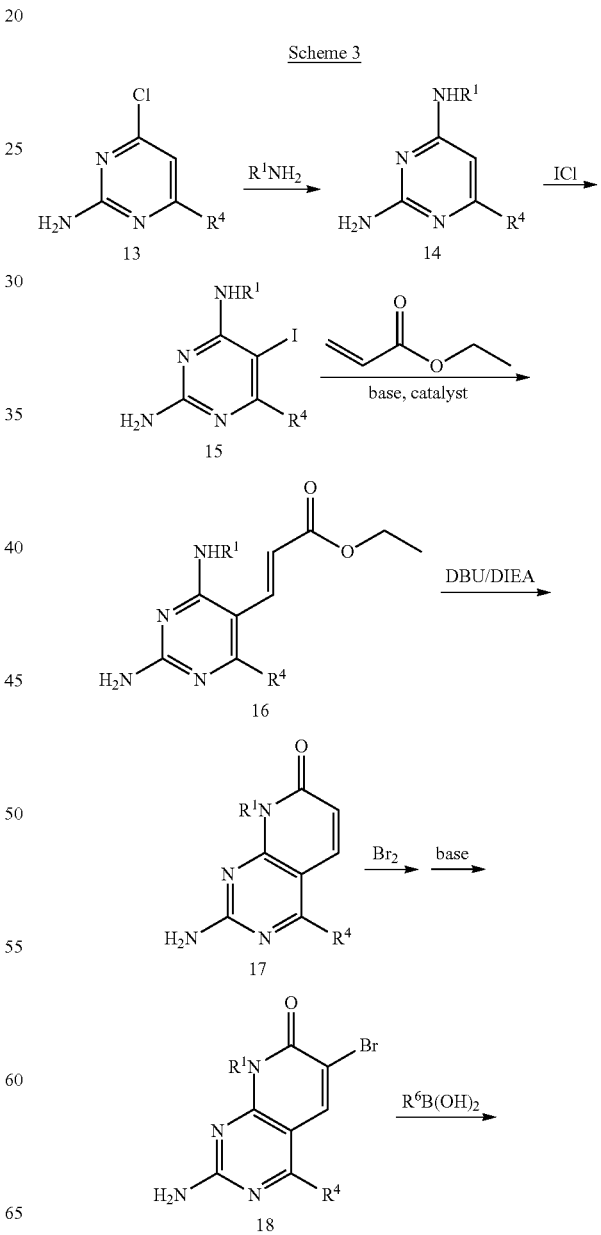

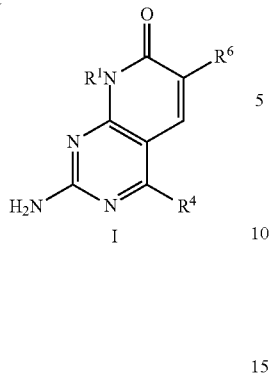

An intermediate of formula 14 is prepared by reacting an intermediate of formula 13 with a primary amine R¹NH₂ in a solvent such as water and with heating. 14 is then treated with iodine monochloride in a solvent such as methanol at around 0° C. and allowed to react for approximately overnight or less as needed for the reaction to go to completion to form 15. After completion the residue is triturated with acetone. The intermediate 15 is then reacted in a solvent, such as DMA, with ethyl acrylate in the presence of a base, such as triethylamine, and in the presence of a catalyst, such as Pd(OAc)₂, and (+)BINAP. The reaction is heated to approximately 100° C. and allowed to react for approximately overnight or less as needed for the reaction to go to completion to form 16. 16 is then optionally purified by column chromatography. A Compound of Formula I can then be prepared from 16 by using the same reaction conditions as described in Scheme 1 (starting at the point of the preparation of 5 from 4).

A compound of the invention where R¹ is optionally substituted alkyl, R⁴ is methyl or ethyl, R⁶ is phenyl or heteroaryl each of which is optionally substituted with 1, 2, 3, 4, or 5 R⁹ groups (as defined in the Summary of the Invention), and R² is hydrogen can alternatively be prepared according to Scheme 4.

Scheme 4

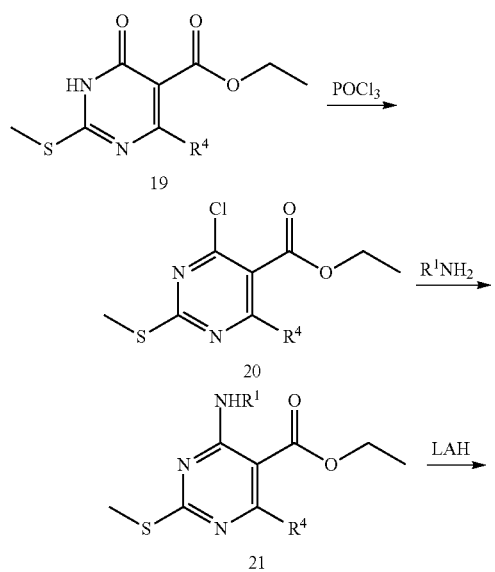

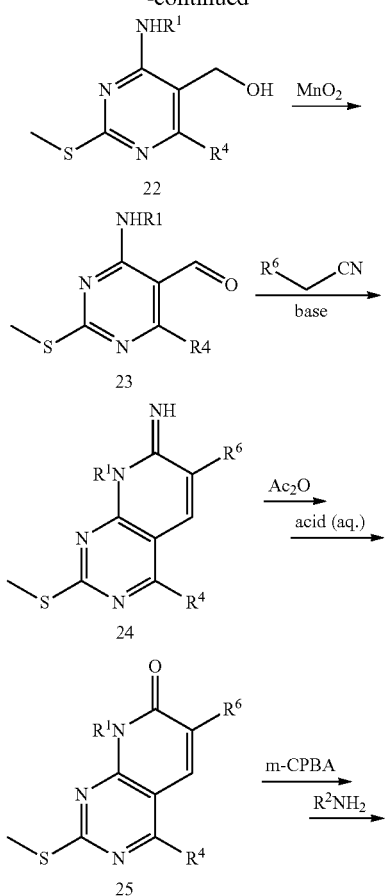

An intermediate of formula 20 is prepared by reacting an intermediate of formula 19 with neat POCl₃ and heating. 20 is then treated with a primary amine R¹NH₂ in a solvent such as water or THF and triethylamine at 0° C. to form 21. After removal of the solvent under reduced pressure, the intermediate 21 is then reacted with lithium aluminum hydride in a solvent such as THF at 0° C. After quenching and aqueous workup, solvent removal provides crystalline 22 without further purification. Treatment of 22 with manganese (II) dioxide in a solvent such as methylene chloride or chloroform at room temperature provides aldehyde 23 upon filtration and solvent removal. A Knovenegal-type condensation with 23 and an arylacetonitrile in the presence of a base such as potassium carbonate or sodium hydroxide in a protic solvent provides the cyclized imine 24. Acetylation of the imine with acetic anhydride is required prior to hydrolysis, which takes place in the presence of aqueous acid and heating to afford 25. Subsequently, 25 can be oxidized to the corresponding sulfone with m-CPBA at room temperature and displaced with ammonium to provide I.

The synthesis of specific compounds is described in WO2007/044813 which is hereby incorporated by reference in its entirety.

Biological Examples

Suitable in vitro assays for measuring PI3K activity and the inhibition thereof by compounds are known in the art. Compounds of Formula I have been tested using one or more of the assays described in Biological Examples 1 and 2. Assays for measurement of in vitro efficacy in the treatment of cancer are known in the art (see also Biological Examples, Example 3, 4, and 5 infra).

Biological Example 1

PI3Kalpha Luciferase-Coupled Chemiluminescence Assay Protocol

PI3Kα activity is measured as the percent of ATP consumed following the kinase reaction using luciferase-luciferiN-coupled chemiluminescence. Reactions were conducted in 384-well white, medium binding microtiter plates (Greiner). Kinase reactions were initiated by combining test compounds, ATP, substrate (PIP2), and kinase in a 20 µL volume in a buffer solution. The standard PI3Kalpha assay buffer was composed of 50 mM Tris, pH 7.5, 1 mM EGTA, 10 mM $MgCl_2$, 1 mM DTT and 0.03% CHAPS. The standard assay concentrations for enzyme, ATP, and substrate were 0.5-1.1 nM, 1 µM, and 7.5 µM, respectively. The reaction mixture was incubated at ambient temperature for approximately 2 h. Following the kinase reaction, a 10 µL aliquot of luciferase-luciferin mix (Promega Kinase-Glo) was added and the chemiluminescence signal measured using a Victor2 plate reader (Perkin Elmer). Total ATP consumption was limited to 40-60% and IC50 values of control compounds correlate well with literature references. PI3Kα was replaced with PI3Kβ, PI3Kδ, or PI3Kγ to determine a compound's activity for the other isoforms of PI3K.

Biological Example 2

Phospho AKT Assay

PC3 cells were seeded on 6-well plates at 150,000 cells/well. Cells were cultured for 3 days, then treated with compounds in serum-free medium for 3 hr. EGF (100 ng/mL) was added for the last 10 min. Cells were lysed in TENN buffer. Phospho T308 Akt and total Akt were quantified by ELISA performed according to the Biosource assay protocol. The readings of phospho Akt were normalized to total Akt readings.

Biological Example 3

Phospho S6 Assay

PC3 cells were seeded on 96-well plates at 8,000 cells/well. For each experiment, cells were seeded and treated in duplicated plates: one plate for phospho S6 CellELISA, and one plate for total S6 CellELISA. Cells were cultured on the plates for 3 days, then treated with compounds in serum-free medium for 3 hr in triplicate. Cells were fixed with 4% formaldehyde, quenched with 0.6% $H_2O_2$, blocked with 5% BSA, incubated with either phospho S6 antibody or total S6 antibody overnight, incubated with goat-anti-rabbit-IgG-HRP for 1 hr, and developed in chemiluminescent substrate.

Biological Example 4

$PIP_3$ Assay

MCF-7 cells grown in 10-cm dishes were starved for 3 hours in DMEM, and then treated with compounds for 20 minutes. In the last 2 minutes of the incubation with the compounds, EGF (100 ng/mL) was added to stimulate the production of PIP3. The medium was aspirated and the cells were scraped with 10% trichloroacetic acid. The lipids were extracted from the pellet after the cell lysates were centrifuged. PIP3 in the cellular lipid extraction was quantified with the AlphaScreen assay in which Grp1-PH is used as the PIP3 specific probe. The amount of cellular PIP3 was calculated from the standard curve of $diC_8$ PI (3,4,5) P3.

Biological Example 5 mTOR/GbL/Raptor (mTORC1) ELISA Assay

The measurement of mTORC 1 enzyme activity was performed in an ELISA assay format following the phosphorylation of 4E-BP1 protein. All experiments were performed in the 384-well format. Generally, 0.5 µl. DMSO containing varying concentrations of the test compound was mixed with 15 µL enzyme solution. Kinase reactions were initiated with the addition of 15 µL of substrates-containing solution. The assay conditions were as follows; 0.2 nM mTORC1, 10 µM ATP and 50 nM NHis-tagged 4E-BP1 in 20 mM Hepes, pH 7.2, 1 mM DTT, 50 mM NaCl, 10 mM $MnCl_2$, 0.02 mg/mL BSA, 0.01% CHAPS, 50 mM β-glycerophosphate. Following an incubation of 120 minutes at ambient temperature, 20 µL of the reaction volume was transferred to a Ni-Chelate-coated 384-well plate. The binding step of the 4E-BP1 protein proceeded for 60 minutes, followed by washing 4 times each with 50 µL of Tris-buffered saline solution (TBS). Anti-phospho-4E-BP1 rabbit-IgG (20 µL, 1:5000) in 5% BSA-TBST (0.2% Tween-20 in TBS) was added and further incubated for 60 minutes. Incubation with a secondary HRP-tagged anti-IgG was similarly performed after washing off the primary antibody (4 washes of 50 µL). Following the final wash step with TBST, 20 µL of SuperSignal ELISA Femto (Pierce Biotechnology) was added and the luminescence measured using an EnVision plate reader.

Biological Example 6

Compound A is a Compound of Formula I and of Table 1.

To test whether a compound of the invention causes apoptotic cell death in PDAC cell lines, a representative subset of cell lines was tested and apoptosis induction was measured by dual staining of cells with PI and Annexin V followed by FACS analysis. Treatment with Compound A resulted in apoptosis induction, which was inversely correlated with GI50, indicating that apoptosis is indeed the most likely mechanism underlying cell death observed in the cell viability assay. See FIG. 1.

Biological Example 7

Compound A is a Compound of Formula I and of Table 1.

Occurrence of cytoplasmic vacuoles in tumor cells treated with dual-targeted inhibitors are consistently observed. Formation of such vacuoles has been described before in the context of induction of autophagy, a cellular survival mechanism that can get activated in response to nutrient deprivation or inhibition of mTOR. A variety of assays, including LC3-I to LC3-II conversion, acridin orange supravital staining, and MDC staining indicate whether treatment of pancreatic cancer cells with a compound of the invention will induce autophagy. The extent of autophagy paralleled induction of apoptosis. See FIGS. 2A and 2B for the induction of apoptosis as determined by FACS analysis following treatment of MiaPaCa2 cells with Compound A as indicated for 72 hours and the induction of autophagy as determined by acridine orange staining and FACS analysis.

Figure 3:
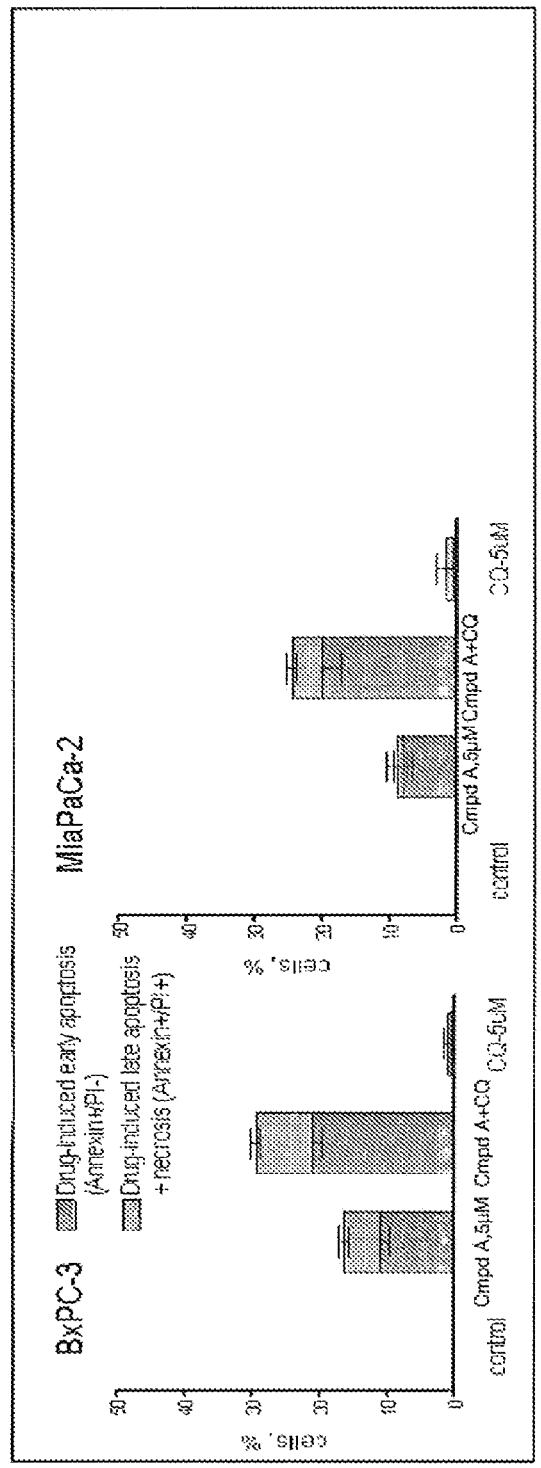
FIG. 3. Enhancement of apoptosis induction by the autophagy inhibitor Choloroquine: Cells were treated with Compound A in the presence or absence of choloroquine (CQ, 5 mM) for 72 hours; apoptosis induction was detected by FACS analysis following PI/Annexin-V staining.

Interestingly, autophagy induction preceded the earliest detectable signs of apoptosis (data not shown), raising the possibility that autophagy protected cells from cell death by apoptosis. We therefore tested whether inhibitors of autophagy or apoptosis could shift the cellular response from autophagy to apoptosis or vice versa. Inhibition of autophagy with 3-MA inhibited autophagy and significantly increased the fraction of cells undergoing apoptosis (data not shown). Similar results were obtained with chloroquine, an anti-malaria agent known to inhibit autophagy (FIG. 3).

Biological Example 8A

Compound A is a compound of Formula I and of Table 1.
Whether autophagy inhibition increased the activity of Compound A in vivo was explored. Xenograft tumors derived from BxPC3 cells were grown subcutaneously as flank tumors in nude mice to a size of 150 mm$^3$. Treatment with Compound A, alone or in combination with choloroquine, was administered for 30 days. Treatment with Compound A along and Compound A in combination with chloroquine was carried out by once daily dosing as indicated. Tumor volume was measured regularly. Tumors were harvested from euthanized mice for protein expression analyses. The combination of Compound A with chloroquine resulted in significant growth inhibition in this model while Compound A alone had no clear growth-inhibitory effect. See FIG. 4A.

Biological Example 8B

Compound A is a Compound of Formula I and of Table 1.
Female 7-9 weeks old Nu/Nu mice (Harlan, FoxN 1/nude) were inoculated s.c. with $10^7$ BxPC-3 cells. Mice were monitored according to the protocol approved by the University of California, San Francisco Institutional Animal Care and Use Committee. When tumors reached about 100 mm$^3$, mice were randomly assigned to one of six treatment groups: vehicle control, Compound A 30 mg/kg, Chloroquine (CQ) 50 mg/kg, Compound A+CQ. Compound A was solubilized in water/10 mM HCl, Compound B was dissolved in water, both drugs were administered by oral gavage once a day 5 times/week. CQ was dissolved in saline and injected i.p daily, 5 times/week. Each treatment regimen was tested in cohorts of eight mice and the dosing was continued for 28 days. Tumor sizes were measured twice weekly in two dimensions using a caliper, tumor size (mm$^3$) was calculated as (length×width$^2$)/2. Animals were monitored for toxicity by measuring body weight twice weekly and monitoring overall activity.

Statistical Analysis.

Dbata are expressed as means+/−standard deviation. Statistical analysis was performed by using Student's t-test (two-tailed). P values of <0.05 were considered significant.

Figure 4:
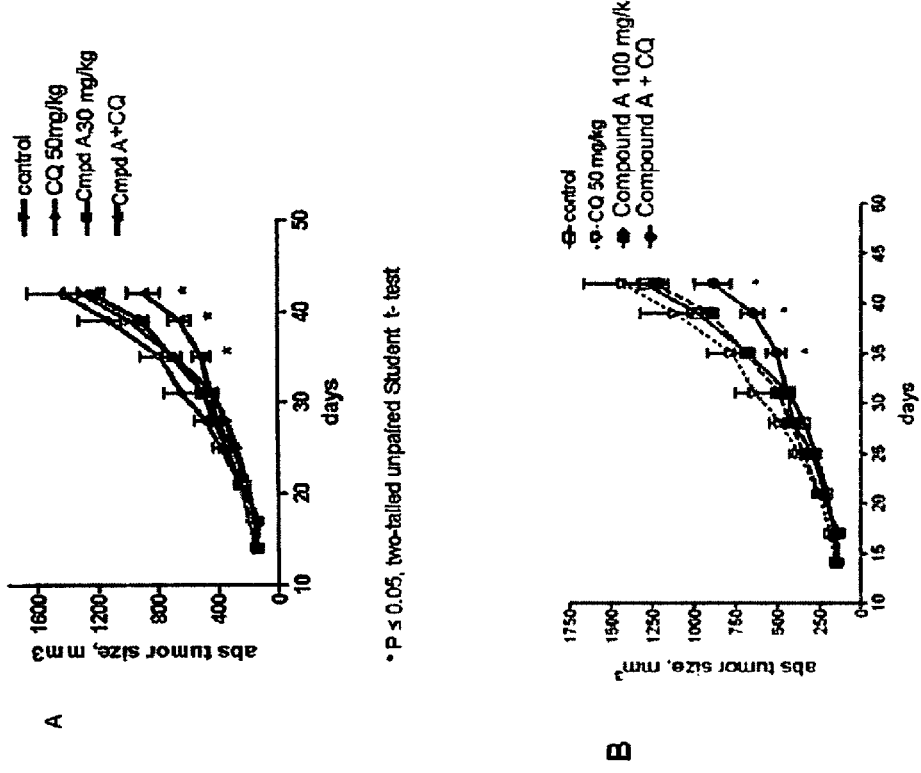
FIG. 4A. Effect of the combination of Compound A and chloroquine (CQ) on tumor growth in a mouse xenograft model of pancreatic cancer.
FIG. 4B. Effect of the combination of Compound A and chloroquine (CQ) on tumor growth in a mouse xenograft model of pancreatic cancer.

As depicted in FIG. 4B, treatment with the combination of Compound A with chloroquine resulted in significant tumor growth delay in this model while Compound A alone had no clear growth-inhibitory effect.

Biological Example 9

Figure 5:
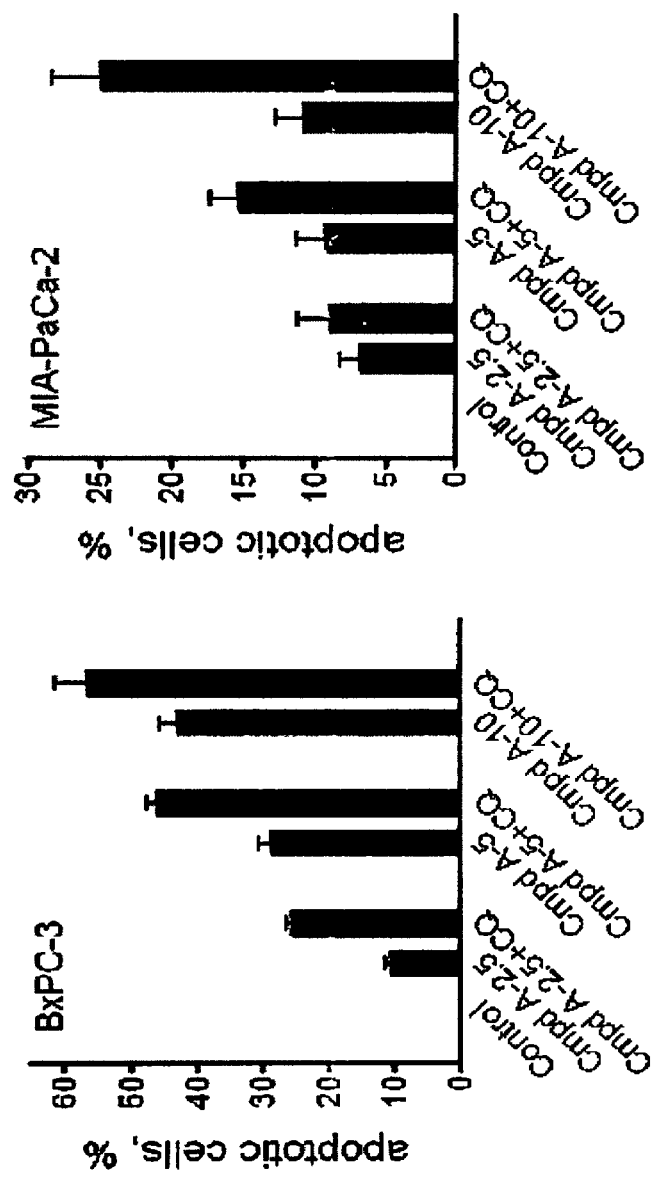
FIG. 5. Enhancement of apoptosis induction by the autophagy inhibitor Choloroquine (CQ).

Compound A is a Compound of Formula I and of Table 1.
Apoptosis triggered by PI3K/mTOR inhibitors in enhanced by autophagy inhibitor chloroquine (CQ). BxPC-3 and MIAPaCa-2 cells were preincubated with CQ for 1 h then treated with different doses of Compound A. Cells were harvested at 72 h post drug treatment, stained with annexin V/PI and analyzed by FACS to determine the percentage of total annexin V positive cells as % of apoptotic cells. Apoptosis of untreated control population was subtracted from the drug treated population to determine the drug-induced apoptosis. Columns, mean of duplicates; bars, SD. For each duplicate, 40,000 cells were acquired. The results were confirmed in three independent experiments. As depicted in FIG. 5, when chloroquine was added to Compound A, apoptotic cell death was significantly enhanced in both cell lines.

The foregoing invention has been described in some detail by way of illustration and example, for purposes of clarity and understanding. The invention has been described with reference to various specific embodiments and techniques. However, it should be understood that many variations and modifications may be made while remaining within the spirit and scope of the invention. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled. All patents, patent applications and publications cited in this application are hereby incorporated by reference in their entirety for all purposes to the same extent as if each individual patent, patent application or publication were so individually denoted.

What is claimed is:

1. A method of treating pancreatic cancer which method comprises administering to a patient a therapeutically effective amount of a compound that is:

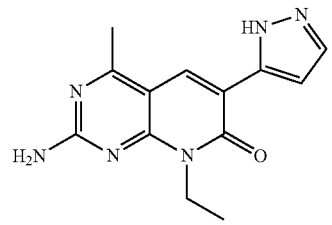 [SMILES: CCn1c(=O)c(-c2ccn[nH]2)cc2c(C)nc(N)nc21]

or a pharmaceutically acceptable salt or composition thereof; in combination with chloroquine.

* * * * *